(12) United States Patent
Hull et al.

(10) Patent No.: US 8,464,925 B2
(45) Date of Patent: *Jun. 18, 2013

(54) METHODS AND APPARATUS FOR DELIVERING TISSUE TREATMENT COMPOSITIONS TO STAPLED TISSUE

(75) Inventors: Joanne Hull, Cincinnati, OH (US); Wells D. Haberstich, Loveland, OH (US); Steven G. Hall, Cincinnati, OH (US); John A. Hibner, Mason, OH (US); Julia J. Hwang, Wayland, MA (US); Yolanda F. Carter, Union, KY (US); Frederick E. Shelton, IV, Hillsboro, OH (US); John B. Schulte, West Chester, OH (US); Rebecca J. Mollere, Loveland, OH (US); Patrick D. Dugan, Madeira, OH (US); Michael D. Cronin, Cincinnati, OH (US); Jerome R. Morgan, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/777,449

(22) Filed: May 11, 2010

(65) Prior Publication Data
US 2011/0278346 A1 Nov. 17, 2011

(51) Int. Cl.
*A61B 17/04* (2006.01)
*A61B 17/10* (2006.01)

(52) U.S. Cl.
USPC ..................... 227/179.1; 227/180.1

(58) Field of Classification Search
USPC ............. 227/175.1–182.1; 222/191; 604/522; 623/11.11, 1.42, 23.72
See application file for complete search history.

(56) References Cited

U.S. PATENT DOCUMENTS

| | | | |
|---|---|---|---|
| 3,937,222 A | * | 2/1976 | Banko ............................ 606/170 |
| 5,271,544 A | | 12/1993 | Fox et al. |
| 5,465,895 A | | 11/1995 | Knodel et al. |
| 5,526,822 A | | 6/1996 | Burbank et al. |

(Continued)

FOREIGN PATENT DOCUMENTS

| EP | 2 189 121 | 5/2010 |
|---|---|---|
| WO | WO 2006/044490 | 4/2006 |
| WO | WO 2006044490 A2 * | 4/2006 |

OTHER PUBLICATIONS

U.S. Appl. No. 12/483,305, filed Jun. 12, 2009, Hibner et al.

(Continued)

*Primary Examiner* — Robert Long
(74) *Attorney, Agent, or Firm* — Frost Brown Todd LLC

(57) ABSTRACT

A surgical stapler includes first and second tissue clamping members and a reservoir configured to hold a tissue treatment composition. The first tissue clamping member is configured to receive a plurality of staples. The second tissue clamping member comprises an anvil configured to form the staples. The reservoir may be provided in a handle portion of the surgical stapler, and a fluid conduit may be used to communicate the tissue treatment composition from the reservoir. An end effector lumen may selectively communicate with the fluid conduit. The lumen may also be in communication with openings to further communicate the tissue treatment composition to tissue or to a scaffold material positioned adjacent to tissue. A reservoir may alternatively be provided in one of the clamping members. A knife member may pierce a housing defining the reservoir, and a resilient member may then urge a tissue treatment composition from the housing.

10 Claims, 12 Drawing Sheets

U.S. PATENT DOCUMENTS

| | | | |
|---|---|---|---|
| 5,533,661 A | 7/1996 | Main et al. | |
| 5,694,951 A | 12/1997 | Bonutti | |
| 5,749,968 A * | 5/1998 | Melanson et al. | 118/300 |
| 6,086,544 A | 7/2000 | Hibner et al. | |
| 6,193,129 B1 | 2/2001 | Bittner et al. | |
| 6,488,197 B1 | 12/2002 | Whitman | |
| 6,964,363 B2 | 11/2005 | Wales et al. | |
| 6,978,921 B2 | 12/2005 | Shelton, IV et al. | |
| 6,990,982 B1 | 1/2006 | Bonutti | |
| 7,115,100 B2 | 10/2006 | McRury et al. | |
| 7,238,195 B2 * | 7/2007 | Viola | 606/219 |
| 7,442,171 B2 | 10/2008 | Stephens et al. | |
| 7,506,791 B2 | 3/2009 | Omaits et al. | |
| 7,607,557 B2 * | 10/2009 | Shelton et al. | 227/175.1 |
| 7,611,473 B2 * | 11/2009 | Boock et al. | 600/564 |
| 7,669,747 B2 * | 3/2010 | Weisenburgh et al. | 227/180.1 |
| 7,673,783 B2 * | 3/2010 | Morgan et al. | 227/180.1 |
| 7,708,180 B2 | 5/2010 | Murray et al. | |
| 7,845,536 B2 * | 12/2010 | Viola et al. | 227/179.1 |
| 2004/0068266 A1 * | 4/2004 | Delmotte | 606/92 |
| 2004/0078090 A1 * | 4/2004 | Binette et al. | 623/23.76 |
| 2004/0097829 A1 * | 5/2004 | McRury et al. | 600/564 |
| 2004/0193071 A1 | 9/2004 | Binette et al. | |
| 2004/0267362 A1 * | 12/2004 | Hwang et al. | 623/13.15 |
| 2005/0038520 A1 * | 2/2005 | Binette et al. | 623/18.11 |
| 2005/0059996 A1 * | 3/2005 | Bauman et al. | 606/215 |
| 2005/0113736 A1 | 5/2005 | Orr et al. | |
| 2005/0125077 A1 * | 6/2005 | Harmon et al. | 623/23.72 |
| 2005/0177249 A1 * | 8/2005 | Kladakis et al. | 623/23.74 |
| 2006/0085033 A1 * | 4/2006 | Criscuolo et al. | 606/219 |
| 2006/0108393 A1 * | 5/2006 | Heinrich et al. | 227/179.1 |
| 2006/0135992 A1 * | 6/2006 | Bettuchi et al. | 606/219 |
| 2006/0271104 A1 * | 11/2006 | Viola et al. | 606/214 |
| 2007/0034668 A1 * | 2/2007 | Holsten et al. | 227/179.1 |
| 2007/0102452 A1 * | 5/2007 | Shelton et al. | 222/191 |
| 2007/0102453 A1 * | 5/2007 | Morgan et al. | 222/191 |
| 2008/0071385 A1 | 3/2008 | Binette et al. | |
| 2008/0140115 A1 | 6/2008 | Stopek | |
| 2008/0214955 A1 | 9/2008 | Speeg et al. | |
| 2008/0234715 A1 * | 9/2008 | Pesce et al. | 606/171 |
| 2008/0286242 A2 * | 11/2008 | Kleinsek et al. | 424/93.7 |
| 2008/0311219 A1 * | 12/2008 | Gosiewska et al. | 424/548 |
| 2009/0092651 A1 * | 4/2009 | Shah et al. | 424/422 |
| 2009/0120994 A1 * | 5/2009 | Murray et al. | 227/180.1 |
| 2010/0127039 A1 * | 5/2010 | Hessler | 227/175.1 |
| 2010/0160819 A1 | 6/2010 | Parihar et al. | |
| 2011/0282324 A1 * | 11/2011 | Kurokawa et al. | 604/514 |
| 2011/0282381 A1 * | 11/2011 | Cronin et al. | 606/213 |
| 2011/0282382 A1 * | 11/2011 | McAlister et al. | 606/213 |
| 2011/0282446 A1 * | 11/2011 | Schulte et al. | 623/11.11 |

OTHER PUBLICATIONS

International Search Report and Written Opinion dated Sep. 13, 2011 for Application No. PCT/US2011/035878.

International Search Report and Written Opinion dated Nov. 23, 2011 for Application No. PCT/US2011/035876.

* cited by examiner

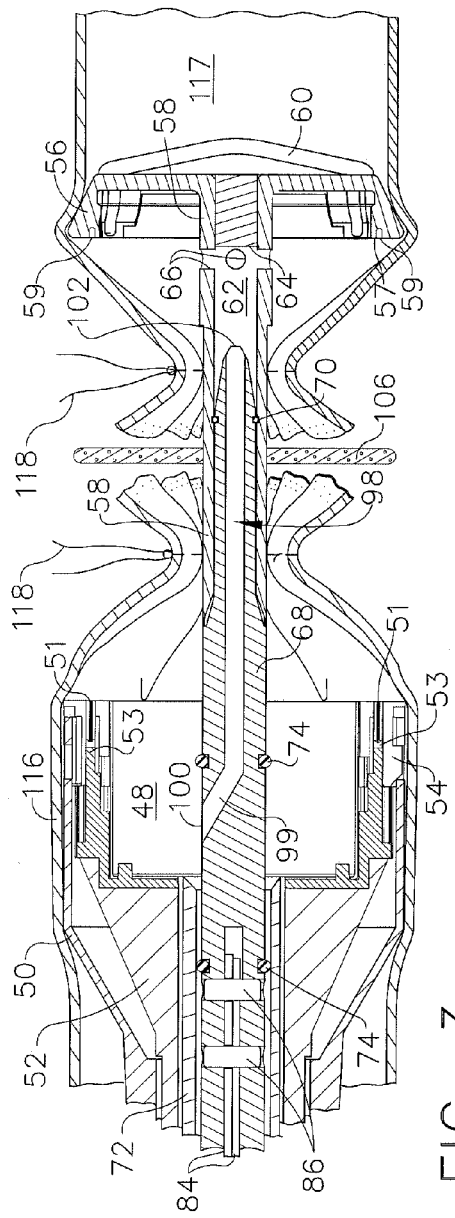
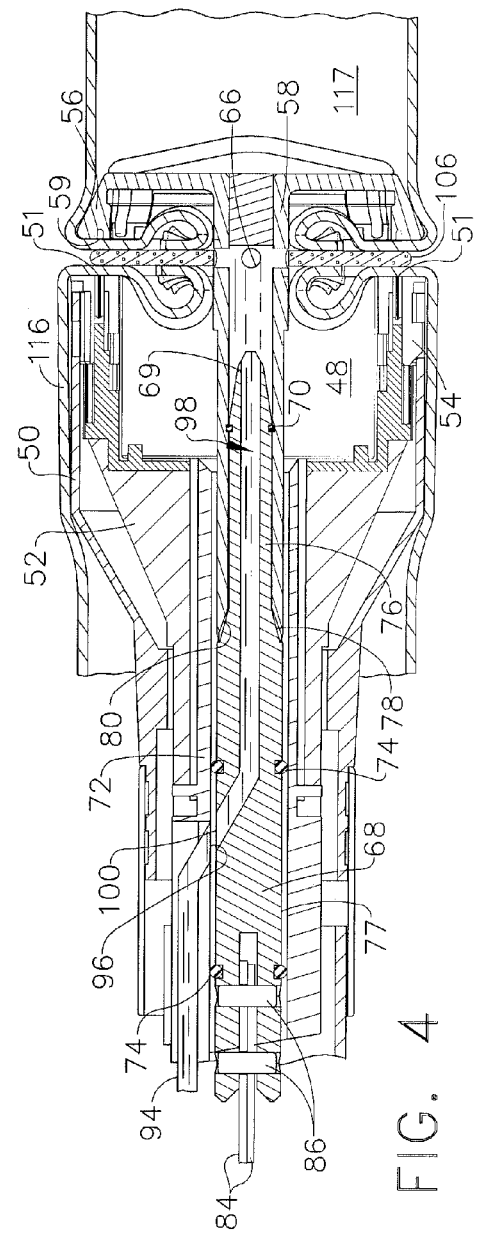
FIG. 3
FIG. 4

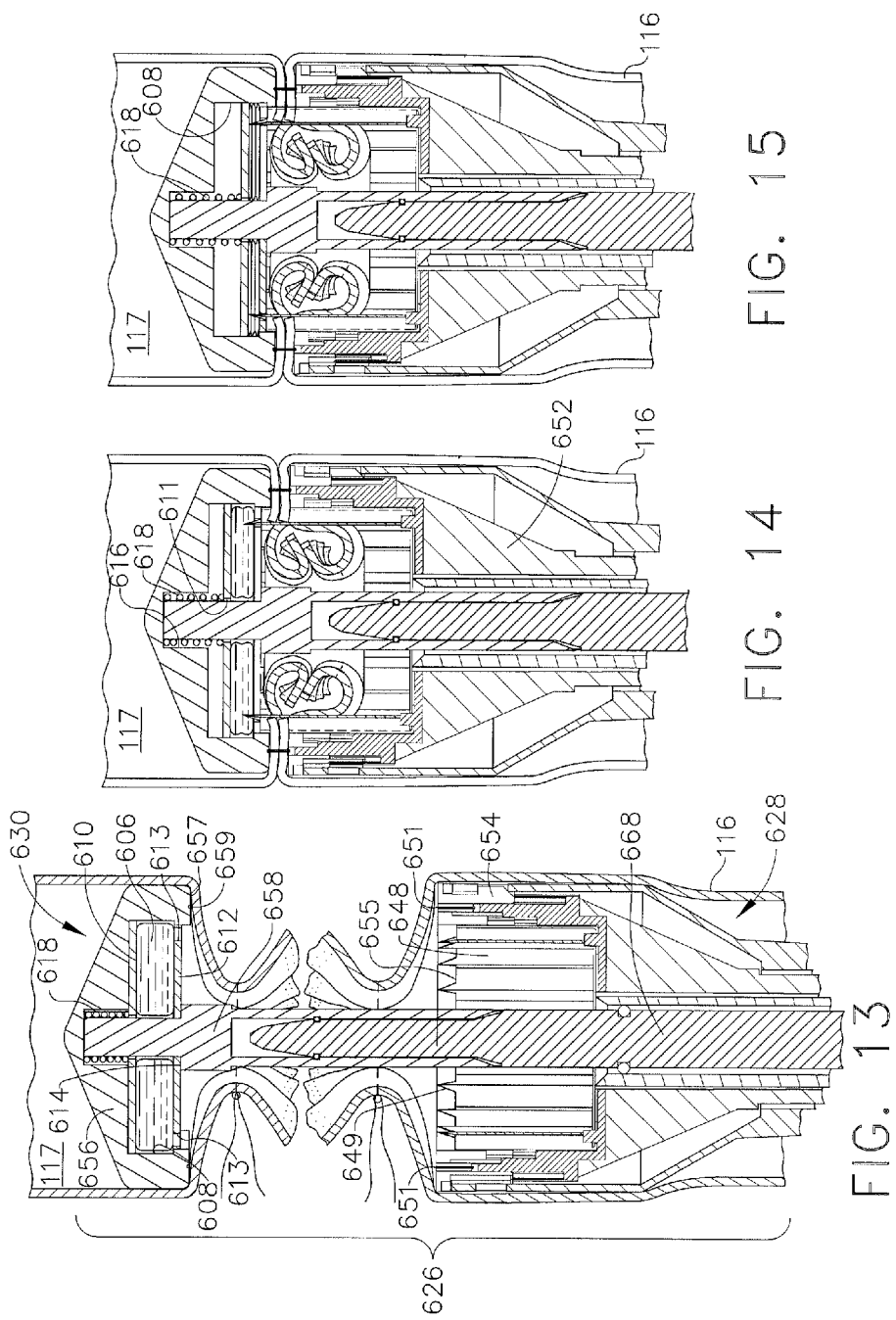

US 8,464,925 B2

METHODS AND APPARATUS FOR DELIVERING TISSUE TREATMENT COMPOSITIONS TO STAPLED TISSUE

BACKGROUND

Promoting and improving tissue healing is an important aspect of some medical treatments and procedures. For instance, promoting and improving tissue healing may lead to quicker recovery times and lessen the opportunity for infection, particularly in a post-surgical context. Some advancements in the medical arts pertaining to systems, methods, and devices to promote and improve tissue healing in patients aim to add active biological components (e.g., tissue particles, stem cells, other types of cells, etc.) to a wound site (e.g., surgical site, accidental trauma site, etc.) or other defect site (e.g., caused by disease or other condition, etc.) to promote tissue regeneration or accelerate tissue healing. When adding biological components to a site, such components may be added independently or as part of a specifically designed matrix or other mixture depending on the condition being treated and goals of the treatment. Some examples of cell-based therapy technology are disclosed in U.S. Pub. No. 2008/0311219, entitled "Tissue Fragment Compositions for the Treatment of Incontinence," published Dec. 18, 2008, the disclosure of which is incorporated by reference herein. Additional examples of cell-based therapy technology are disclosed in U.S. Pub. No. 2004/0078090, entitled "Biocompatible Scaffolds with Tissue Fragments," published Apr. 22, 2004, the disclosure of which is incorporated by reference herein. Additional examples of cell-based therapy technology are disclosed in U.S. Pub. No. 2008/0071385, entitled "Conformable Tissue Repair Implant Capable of Injection Delivery," published Mar. 20, 2008, and issued Jan. 25, 2011 as U.S. Pat. No. 7,875,296, the disclosure of which is incorporated by reference herein.

Regardless of how the active biological components are delivered or applied to a site, the biological components must first be obtained and prepared. One approach for obtaining such biological components is to harvest the desired components from a healthy tissue specimen (e.g., in an adult human). Examples of devices and associated methods for collecting and processing harvested tissue are disclosed in U.S. Pub. No. 2004/0193071, entitled "Tissue Collection Device and Methods," published Sep. 30, 2004, and issued Sep. 14, 2010 as U.S. Pat. No. 7,794,408, the disclosure of which is incorporated by reference herein. Additional examples of devices and associated methods for collecting and processing harvested tissue are disclosed in U.S. Pub. No. 2005/0038520, entitled "Method and Apparatus for Resurfacing an Articular Surface," published Feb. 17, 2005, the disclosure of which is incorporated by reference herein. Additional examples of devices and associated methods for collecting and processing harvested tissue are disclosed in U.S. Pat. No. 7,611,473, entitled "Tissue Extraction and Maceration Device," issued Nov. 3, 2009, the disclosure of which is incorporated by reference herein. Additional examples of devices and associated methods for collecting and processing harvested tissue are disclosed in U.S. Pub. No. 2008/0234715, entitled "Tissue Extraction and Collection Device," published Sep. 25, 2008, and issued Oct. 11, 2011 as U.S. Pat. No. 8,034,003, the disclosure of which is incorporated by reference herein. Additional examples of devices and associated methods for processing harvested tissue are disclosed in U.S. Pub. No. 2005/0125077, entitled "Viable Tissue Repair Implants and Methods of Use," published Jun. 9, 2005, and issued Mar. 8, 2011 as U.S. Pat. No. 7,901,461, the disclosure of which is incorporated by reference herein. Additional examples of devices and associated methods for collecting and processing harvested tissue are disclosed in U.S. Pat. No. 5,694,951, entitled "Method for Tissue Removal and Transplantation," issued Dec. 9, 1997, the disclosure of which is incorporated by reference herein. Additional examples of devices and associated methods for collecting and processing harvested tissue are disclosed in U.S. Pat. No. 6,990,982, entitled "Method for Harvesting and Processing Cells from Tissue Fragments," issued Jan. 31, 2006, the disclosure of which is incorporated by reference herein. Additional examples of devices and associated methods for collecting and processing harvested tissue are disclosed in U.S. Pat. No. 7,115,100, entitled "Tissue Biopsy and Processing Device," issued Oct. 3, 2006, the disclosure of which is incorporated by reference herein.

Once harvested and suitably processed (e.g., incorporated with a scaffold, etc.), biological material such as tissue fragments may be applied to a wound site or other type of site within the human body in a variety of ways. Various methods and devices for applying such biological material are disclosed in one or more of the U.S. patent references cited above. Additional methods and devices for applying such biological material are disclosed in U.S. Pub. No. 2005/0113736, entitled "Arthroscopic Tissue Scaffold Delivery Device," published May 26, 2005, the disclosure of which is incorporated by reference herein.

While a variety of devices and techniques may exist for harvesting, processing, and applying biological components from a tissue specimen, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

FIG. 3 depicts a partial cross-sectional view of the end effector portion of the stapler shown in FIG. 1, positioned in a pair of tissue lumens to be joined in an anastomosis, with the scaffold of FIG. 5 positioned between the clamping members;

FIG. 4 depicts a partial cross-sectional view of the stapler shown in FIG. 3, with the end effector closed to clamp the ends of the tissue lumens and the scaffold between the clamping members;

FIG. 13 depicts a partial cross-sectional view of the end effector portion of another exemplary circular surgical stapler positioned in a pair of tissue lumens to be joined in an anastomosis, with a rupturable fluid housing located in the second clamping member of the end effector;

FIG. 14 depicts a partial cross-sectional view of the stapler shown in FIG. 13, with the stapler in a fired position to fasten the tissue lumens together, rupture the fluid housing, and cut the tissue lumens;

FIG. 15 depicts a partial cross-sectional view of the stapler shown in FIG. 13, with the stapler having been re-fired so as to further cut the tissue into smaller fragments, and with the fluid housing emptied;

Figure 1:
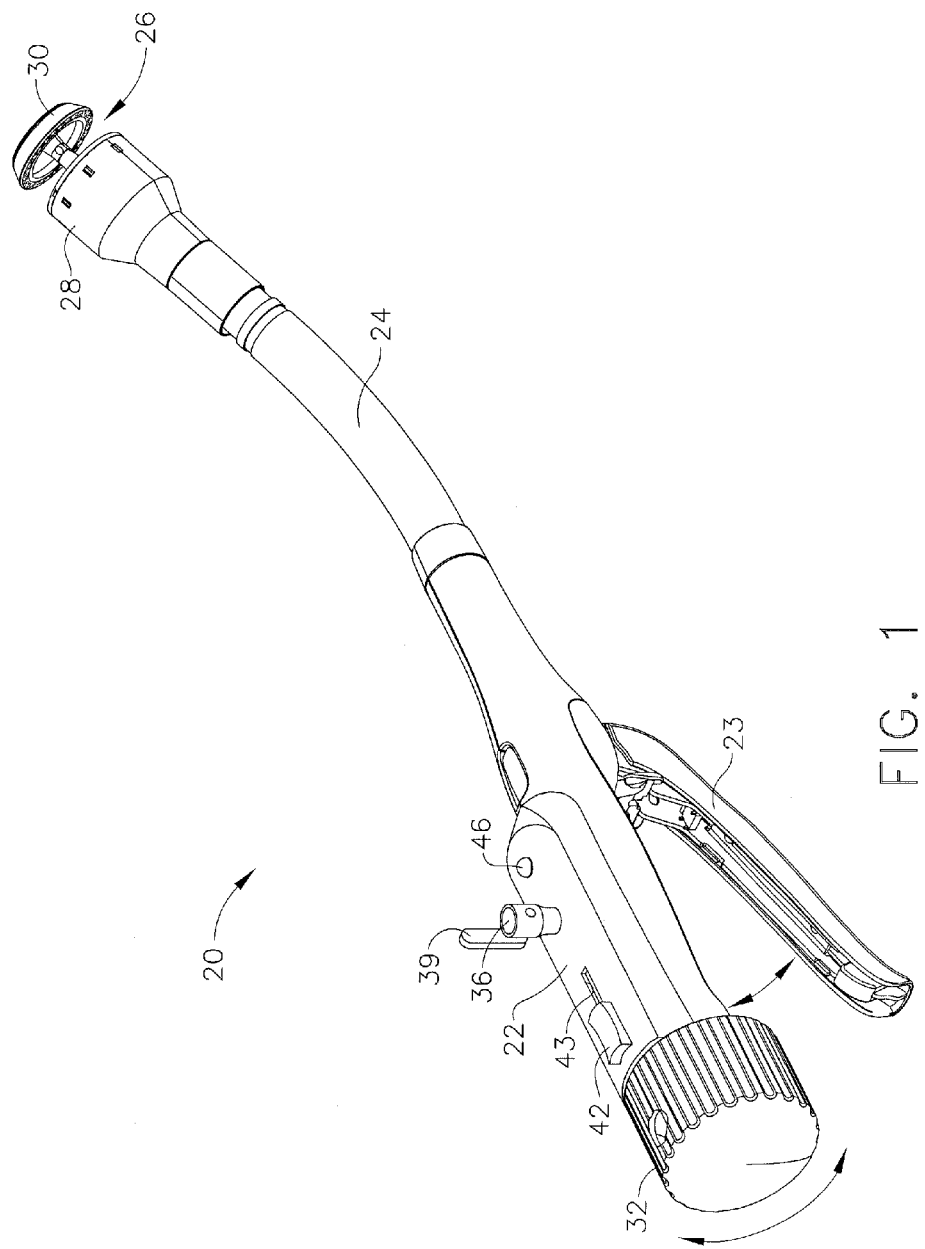
FIG. 1 depicts a perspective view of an exemplary circular surgical stapler having a tissue mincing chamber.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

I. Exemplary Tissue Treatment Compositions for Use with Surgical Staplers

Surgical stapling devices may be used to clamp onto tissue, place a plurality of staples in an array into the tissue, and, in some instances, cut the tissue within the array of staples. Such stapling devices may apply staples along a path that is circular, linear, arcuate, or any other desired shape; and may be used, for example, to resect or transect tissue, to perform an anastomosis on luminal structures such as intestines, or in any of a variety of other surgical procedures. Examples shown and described herein provide a tissue treatment composition such as a medical fluid having one or more healing agents to the stapled tissue, such as at the staple line (e.g., where the fasteners extend into the tissue), at the cut line (e.g., where the tissue is cut), and/or elsewhere. The medical fluid may include any of a variety of biocompatible materials that accelerate tissue healing, promote tissue regeneration, and/or provide other results. As used herein, the terms "tissue treatment composition," "tissue repair composition," and "medical fluid" should be read interchangeably. It should also be understood that a tissue treatment composition or medical fluid as referred to herein may have any suitable consistency, including but not limited to the consistency of a slurry.

A medical fluid as referred to herein may be derived from any biocompatible material, including but not limited to synthetic or natural polymers. The consistency of the medical fluid may be viscous, or gel-like, that of a slurry composed of microparticles, or any other suitable consistency. By way of example only, any fluid consistency that may permit injection through a catheter may be used. The medical fluid may also provide adhesive characteristics, such that once it is injected at a target site (e.g., into a fistula), the fluid coagulates or gels (e.g., allowing for a plug to be retained within a fistula). The medical fluid of the present example is also able to support cell migration and proliferation such that healing at a target site in a patient can occur. The fluid is suitable to be mixed with biological materials. Examples of medical fluid components include but are not limited to thrombin, platelet poor plasma (PPP) platelet rich plasma (PRP), starch, chitosan, alginate, fibrin, polysaccharide, cellulose, collagen, gelatin-resorcin-formalin adhesive, oxidized cellulose, mussel-based adhesive, poly (amino acid), agarose, amylose, hyaluronan, polyhydroxybutyrate (PHB), hyaluronic acid, poly(vinyl pyrrolidone) (PVP), poly(vinyl alcohol) (PVA), polylactide (PLA), polyglycolide (PGA), polycaprolactone (PCL), and their copolymers, VICRYL® (Ethicon, Inc., Somerville, N.J.), MONOCRYL material, PANACRYL (Ethicon, Inc., Somerville, N.J.), and/or any other material suitable to be mixed with biological material and introduced to a wound or defect site, including combinations of materials. Other suitable compounds, materials, substances, etc., that may be used in a medical fluid will be apparent to those of ordinary skill in the art in view of the teachings herein.

By way of example only, one or more components in a medical fluid or tissue treatment composition may comprise at least one viable tissue fragment having one or more viable cells that, once applied, can proliferate and integrate with tissue at a target site in a patient. For instance, viable cells may migrate out of a tissue particle and populate a scaffold material, which may be positioned at a target site in a patient. Such tissue fragments may have been harvested from the same patient in whom they are reapplied; or may have been harvested from another person or source. The tissue fragments may comprise autogenic tissue, allogenic tissue, xenogenic tissue, mixtures of any of the foregoing, and/or any other type(s) of tissue. The tissue fragments may include, for example, one or more of the following tissues or tissue components: stem cells, cartilage tissue, meniscal tissue, ligament tissue, tendon tissue, skin tissue, muscle tissue (e.g., from the patient's thigh, etc.), periosteal tissue, pericardial tissue, synovial tissue, fat tissue, bone marrow, bladder tissue, umbilical tissue, embryonic tissue, vascular tissue, blood and combinations thereof. Of course, any other suitable type of tissue may be used, including any suitable combination of tissue types. In some versions, the type of tissue used is selected from a tissue type most resembling the tissue at, near, or surrounding the target site (e.g., fistula, etc.).

Tissue for providing at least one viable tissue fragment may be obtained using any of a variety of tissue biopsy devices or using other types of tissue harvesting devices or techniques. Exemplary biopsy devices include those taught in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2007/0118048, entitled "Remote Thumbwheel for a Surgical Biopsy Device," published May 24, 2007, and issued Oct. 28, 2008 as U.S. Pat. No. 7,442,171; U.S. Pub. No. 2008/0214955, entitled "Presentation of Biopsy Sample by Biopsy Device," published Sep. 4, 2008; U.S. Non-Provisional patent application Ser. No. 12/337,942, entitled "Biopsy Device with Central Thumbwheel," filed Dec. 18, 2008, and published Jun. 24, 2010 as U.S. Pub. No. 2010/0160819; and U.S. Non-Provisional patent application Ser. No. 12/483,305, entitled "Tetherless Biopsy Device with Reusable Portion," filed Jun. 12, 2009, and issued Jun. 26, 2012 as U.S. Pat. No. 8,206,316. The disclosure of each of the above-cited U.S. patents, U.S. patent application Publications, and U.S. Non-Provisional patent applications is incorporated by reference herein. Such biopsy devices may be used to extract a plurality of tissue specimens from one or more sites in a single patient. It should also be understood that any suitable device described in any other reference that is cited herein may be used to harvest tissue. Other examples will be apparent to those of ordinary skill in the art in view of the teachings herein. Tissue harvesting sites may include the same sites in which tissue is reapplied as part of a treatment. In addition or in the alternative, tissue may be harvested from one site and then reapplied at some other site as part of a treatment. In some versions, the tissue is reapplied in the same patient from whom the tissue was originally harvested. In some other versions, the tissue is applied in a patient who is different from the patient from whom the tissue was originally harvested.

A tissue specimen may be obtained under aseptic conditions, and then processed under sterile conditions to create a suspension having at least one minced, or finely divided, tissue fragment. In other words, harvested tissue may be diced, minced or morcellated, and/or otherwise processed. Harvested tissue specimens may be minced and otherwise processed in any of a variety of ways. For instance, examples of tissue mincing and processing are described in U.S. Pub. No. 2004/0078090, the disclosure of which is incorporated by reference herein. Other examples will be apparent to those of ordinary skill in the art in view of the teachings herein. In order to ensure viability of the tissue, agitators or other features of a mincing and/or mixing device may be designed to sever and mix (rather than crush or compress) the tissue. In some settings, tissue specimens may be minced and/or mixed in a standard cell culture medium, either in the presence or absence of serum. Tissue fragments may also be contacted with a matrix-digesting enzyme to facilitate cell migration out of an extracellular matrix surrounding the cells. Suitable matrix-digesting enzymes that may be used in some settings include, but are not limited to, collagenase, chondroitinase, trypsin, elastase, hyaluronidase, peptidase, thermolysin, and protease. The size of each tissue fragment may vary depending on the target location, method for delivering the treatment composition to the target site, and/or based on various other considerations. For example, the tissue fragment size may be chosen to enhance the ability of regenerative cells (e.g., fibroblasts) in the tissue fragments to migrate out of the tissue fragments, and/or to limit or prevent the destruction of cell integrity. In some settings, ideal tissue fragments are between approximately 200 microns and approximately 500 microns in size. As another merely illustrative example, ideal tissue fragments may be sized within the range of approximately 0.05 mm$^3$ and approximately 2 mm$^3$; or more particularly between approximately 0.05 mm$^3$ and approximately 1 mm$^3$. Of course, various other tissue fragment sizes may be ideal in various different settings.

In some versions, a medical fluid may comprise minced tissue fragments suspended in a biocompatible carrier. Suitable carriers may include, for example, a physiological buffer solution, a flowable gel solution, saline, and water. In the case of gel solutions, the tissue repair composition may be in a flowable gel form prior to delivery at the target site, or may form a gel and remain in place after delivery at the target site. Flowable gel solutions may comprise one or more gelling materials with or without added water, saline, or a physiological buffer solution. Suitable gelling materials include biological and synthetic materials. Exemplary gelling materials include the following: proteins such as collagen, collagen gel, elastin, thrombin, fibronectin, gelatin, fibrin, tropoelastin, polypeptides, laminin, proteoglycans, fibrin glue, fibrin clot, platelet rich plasma (PRP) clot, platelet poor plasma (PPP) clot, self-assembling peptide hydrogels, Matrigel or atelocollagen; polysaccharides such as pectin, cellulose, oxidized regenerated cellulose, chitin, chitosan, agarose, or hyaluronic acid; polynucleotides such as ribonucleic acids or deoxyribonucleic acids; other materials such as alginate, cross-linked alginate, poly(N-isopropylacrylamide), poly(oxyalkylene), copolymers of poly(ethylene oxide)-poly(propylene oxide), poly(vinyl alcohol), polyacrylate, or monostearoyl glycerol co-Succinate/polyethylene glycol (MGSA/PEG) copolymers; and combinations of any of the foregoing. In addition to providing a flowable carrier solution for tissue fragments, a gelling agent(s) may also act as an adhesive that anchors the tissue repair composition at the target site. In some versions, an additional adhesive anchoring agent may be included in the tissue repair composition or medical fluid. Also, one or more cross-linking agents may be used in conjunction with one or more gelling agents in order to cross-link the gelling agent.

The concentration of tissue fragments in a carrier and/or one or more medical fluid components may vary depending on the target site location, method for delivering the treatment composition to the target site, and/or for various other reasons. By way of example, the ratio of tissue fragments to carrier (by volume) may be in the range of about 2:1 to about 6:1, or in the range of about 2:1 to about 3:1. The medical fluid may also include one more additional healing agents, such as biological components that accelerate healing and/or tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Similarly, in some versions where a scaffold plug is used in conjunction with a tissue repair composition, one or more of these additional biological components or additional treatment components may be provided on and/or within the scaffold plug. Some examples described herein may also include one or more adhesive agents in conjunction with viable tissue fragments.

As noted above, the harvested tissue may be combined with a scaffold material and/or other substances as part of a medical fluid, as described herein, for administration to the patient. To the extent that tissue is incorporated with a scaffold material, it should be understood that any suitable material or combination of materials may be used to provide a scaffold. By way of example only, scaffold material may include a natural material, a synthetic material, a bioabsorbable polymer, a non-woven polymer, other types of polymers, and/or other types of materials or combinations of materials. Examples of suitable biocompatible materials include starch, chitosan, cellulose, agarose, amylose, lignin, hyaluronan, alginate, hyaluronic acid, fibrin glue, fibrin clot, collagen gel, gelatin-resorcin-formalin adhesive, platelet rich plasma (PRP) gel, platelet poor plasma (PPP) gel, Matrigel, Monostearoyl Glycerol co-Succinate (MGSA), Monostearoyl Glycerol co-Succinate/polyethylene glycol (MGSA/PEG) copolymers, laminin, elastin, proteoglycans, polyhydroxybutyrate (PHB), poly(vinyl pyrrolidone) (PVP), polylactide (PLA), polyglycolide (PGA), polycaprolactone (PCL), and their copolymers, non-woven VICRYL® (Ethicon, Inc., Somerville, N.J.), MONOCRYL material, fibrin, non-woven poly-L-lactide, and non-woven PANACRYL (Ethicon, Inc., Somerville, N.J.). Polymers may include aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, poly(propylene fumarate), polyurethane, poly(ester urethane), poly(ether urethane), and blends and copolymers thereof. Suitable synthetic polymers for use in examples described herein may also include biosynthetic polymers based on sequences found in collagen, laminin, glycosaminoglycans, elastin, thrombin, fibronectin, starches, poly(amino acid), gelatin, alginate, pectin, fibrin, oxidized cellulose, chitin, chitosan, tropoelastin, hyaluronic acid, silk, ribonucleic acids, deoxyribonucleic acids, polypeptides, proteins, polysaccharides, polynucleotides, and combinations thereof. Other suitable materials or combinations of materials that may be used will be apparent to those of ordinary skill in the art in view of the teachings herein. It should also be understood that tissue mixed with a scaffold material may have any suitable particle size, and that the resulting mixture may at least initially have the consistency of a slurry or have any other suitable consistency. In some versions, the tissue particles include an effective amount of viable cells that can migrate out of the tissue particle and populate the scaffold. The term "viable," as used herein, should be understood to include a tissue sample having one or more viable cells.

In some versions, one or more components in a medical fluid or tissue treatment composition comprise one or more healing agents that promote tissue regeneration at a target site (e.g., within a fistula) and/or accelerate tissue healing at the target site. Healing agents may include any of a variety of biocompatible materials that accelerate tissue healing and/or promote tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Some examples described herein may also include one or more adhesive agents in conjunction with viable tissue fragments.

Examples described herein relate to the repair (e.g., anastomosis) of lumens in a patient. In particular, examples described herein include devices used in at least part of a process to deliver tissue treatment compositions or medical fluid into a lumen at an anastomosis site. In some versions, a tissue treatment composition is delivered to the stapled tissue at a staple line, such as through a fluid conduit within the stapler. In some other versions, a tissue treatment composition is released from a rupturable housing which, for example, may be located in or on the end effector of the stapler and be ruptured by being clamped between the stapling head and anvil, by the staples, and/or by a cutting knife in the stapler. Furthermore, the tissue treatment composition may be provided on a scaffold positionable between the stapling head and the anvil of the stapler. Various examples of such ways in which a medical device may incorporate a tissue treatment composition will be described in greater detail below, while additional examples will be apparent to those of ordinary skill in the art in view of the teachings herein. While these examples are described in the context of staplers, it should be understood that the following teachings may be readily applied to various other types of medical devices, including but not limited to surgical clip appliers. For example, the teachings herein may be applied to other types of surgical fastener devices, such as surgical tackers used in various procedures such as hernia repair using a hernia prosthesis (e.g., a hernia mesh). By way of further example, the teachings herein may be applied to devices used to cut and coagulate tissue, such as those which use RF or ultrasonic energy. Various suitable ways in which the following teachings may be applied to other types of medical devices will be apparent to those of ordinary skill in the art. Similarly, while the below examples are described in the context of end-to-end anastamoses of tissue lumens, it should be understood that the following teachings may be readily applied to various other types of surgical procedures. Various types of surgical procedures in which the following teachings may be incorporated will be apparent to those of ordinary skill in the art.

As used herein, the term "fluid communication" (or in some contexts "communication") means that there is a path or route through which fluid (gas, liquid or other flowable material) may flow between two components, either directly or through one or more intermediate components. Similarly, the term "conduit" encompasses a conduit within or integrated with a valve. In other words, fluid communication between two components means that fluid can flow from one component to another but does not exclude an intermediate component (e.g., a valve, etc.) between the two recited components that are in fluid communication. Similarly, two or more components may be in mechanical "communication" with each other even if intermediate components are interposed between those two or more components.

II. Exemplary Surgical Stapler Having Reservoir for Housing Tissue Treatment Composition FIG. 1 depicts an exemplary surgical stapler (20) of the type that is used to create an end-to-end anastomosis, such as in the intestinal tract following a resection. Stapler (20) may be similar in construction to that shown in, for example, U.S. Pat. No. 5,533,661, entitled "Sealing Means for Endoscopic Surgical Anastomosis Stapling Instrument," issued Jul. 9, 1996, the disclosure of which is incorporated by reference herein; and/or U.S. Pub. No. 2009/0120994, entitled "Surgical Fastening Device with Initiator Impregnation of a Matrix or Buttress to Improve Adhesive Application," published May 14, 2009, and issued May 4, 2010 as U.S. Pat. No. 7,708,180, the disclosure of which is incorporated by reference herein. It should be noted that the apparatus and methods described herein may be incorporated into or otherwise used with other types of surgical staplers such as a linear stapler. Linear staplers are shown and described in, for example, in U.S. Pat. No. 5,465,895, entitled "Surgical Stapler Instrument," issued Nov. 14, 1995, the disclosure of which is incorporated by reference herein; U.S. Pat. No. 6,964,363, entitled "Surgical Stapling Instrument having Articulation Joint Support Plates for Supporting a Firing Bar," issued Nov. 15, 2005, the disclosure of which is incorporated by reference herein; and U.S. Pat. No. 6,978,921, entitled "Surgical Stapling Instrument Incorporating an E-beam Firing Mechanism," issued Dec. 27, 2005, the disclosure of which is incorporated by reference herein.

Circular stapler (20) of the present example has a handle (22), a shaft (24) extending distally therefrom, and a circular end effector (26) at a distal end of the shaft (24). Circular end effector (26) includes a first tissue clamping member (28) (or stapling head) having a plurality of staples disposed therein in one or more arrays, and a second tissue clamping member (30) comprising an anvil for forming the staples. At least one of the tissue clamping members (28, 30) is moveable between an open position for receiving tissue between the clamping members (28, 30), and a closed position for clamping and stapling tissue between the clamping members (28, 30). In the present example, second clamping member (30) is movable with respect to first clamping member (28). Also in the present example, an elongate shaft extends between the first and second clamping members (28, 30). In this exemplary embodiment, the elongate shaft comprises an anvil shaft (58), which receives a distal end portion of a post member (68) such that the second clamping member (30) may be pulled towards the first clamping member (28) by the post member (68), as further described herein. In some other versions, the anvil shaft may be received within the distal end of a hollow shaft extending through the first clamping member.

An actuatable firing trigger (23) is provided in order to fire stapler (20). In the present example as shown in FIG. 1, the firing trigger (23) is pivotally connected to the handle (22), and is depicted in the open position. Trigger (23) may be moved (i.e., pivoted) to a closed position adjacent handle (22) in order to fire stapler (20). It should be understood that trigger (23) is merely one example of a feature that may be used to fire stapler (20), and that a variety of other types of features or components may be provided to fire stapler (20).

As further described herein, the second tissue clamping member (30) is operably connected to a rotatable clamping knob (32) located on the handle (22). Rotation of clamping knob (32) moves second tissue clamping member (30) to the closed position shown in FIG. 4. Rotation of clamping knob (32) in the opposite direction moves the second clamping member (30) back to the open position (FIG. 3). Of course, a variety of alternative features or components may be provided to move second clamping member (30) between open and closed positions.

Figure 2A:
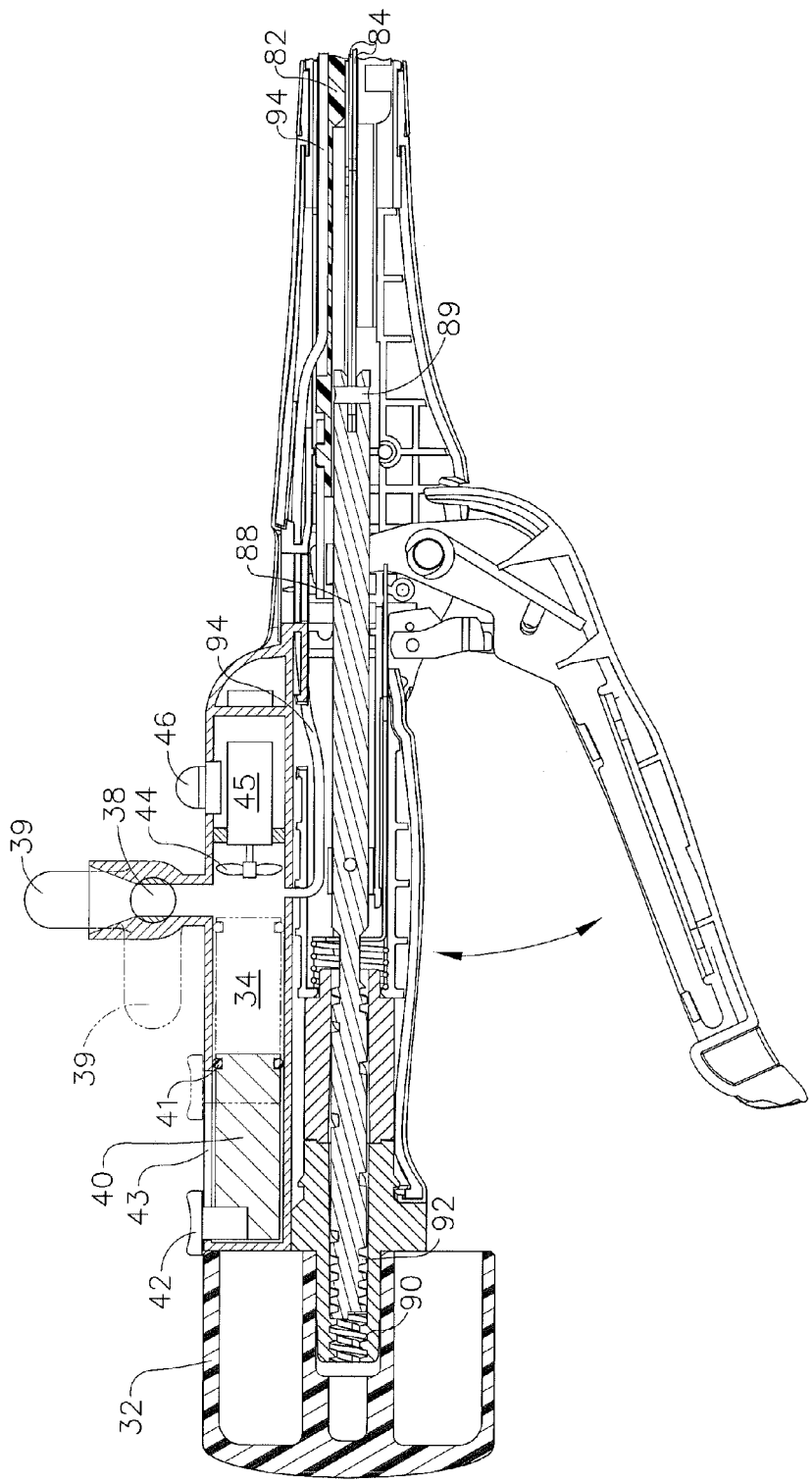
FIG. 2A depicts a partial cross-sectional view of a proximal portion of the stapler shown in FIG. 1.

Stapler (20) of the present example also include a reservoir (34) for containing a tissue treatment composition comprising one or more tissue healing agents (e.g., one or more viable tissue fragments suspended in a carrier). In particular, as shown in FIG. 2A, reservoir (34) is provided in the handle (22) of the stapler (20) in the present example. It should be understood, though, that the reservoir may be located elsewhere within the stapler (20) or even external to the stapler (20). For instance, in some versions, the reservoir is positioned externally of the handle (22), and is operatively connected to the handle (22) or other portion of the stapler (20) for delivering the tissue treatment composition to the staple line and/or tissue cut line.

While the stapler (20) may be provided to an end-user with the tissue treatment composition pre-loaded in the reservoir (34), stapler (20) of the present example includes an inlet port (36) through which the reservoir (34) may be supplied with a tissue treatment composition (or components of the composition). For example, one or more tissue healing agents, such as viable tissue fragments, and a carrier (e.g., saline or water) and/or scaffold material, etc., may be injected into the reservoir (34) through the inlet port (36). Alternatively, the stapler (20) may be pre-loaded with some components of the tissue treatment composition (e.g., a carrier), while other components such as viable tissue fragments are injected into the reservoir (34) at the time of use. A valve (38) for selectively closing inlet port (36) may also be provided, as shown schematically in FIG. 2A, such that the inlet port (36) may be closed after the reservoir (34) has been filled with a tissue treatment composition. In the present example, a valve lever (39) is provided in order to open and close valve 38. As an alternative to employing a valve on inlet port (36), a self-sealing septum may be positioned over inlet port (36) such that the tissue treatment composition (or components thereof) may be injected into reservoir (34) through the self-sealing septum. Other suitable ways in which a medical fluid may be communicated to reservoir (34) and how medical fluid may be retained in reservoir (34) will be apparent to those of ordinary skill in the art in view of the teachings herein.

As further described herein, at least one fluid conduit may also be provided in order to selectively deliver tissue healing agent(s) from the reservoir (34) to a location between the first and second clamping members at the time of clamping and stapling (and/or immediately prior to, and/or immediately after clamping and stapling.

The one or more healing agents inserted into reservoir (34) may comprise one or more viable tissue fragments such as, for example, a muscle tissue specimen from a donor (autologous, allogeneic, and/or xenogeneic) using appropriate harvesting tools. Of course, any suitable tissue type may be used in addition to or in lieu of muscle tissue. In order to facilitate delivery of the tissue fragments to the staple and/or cut line, as well as to facilitate migration of viable cells from the tissue fragments, the tissue specimen(s) may be finely minced into small fragments before being inserted into the reservoir (34). Tissue mincing may be accomplished as the tissue is collected, or alternatively, the tissue may be minced after being harvested and collected from a donor. Mincing the tissue can be accomplished by a variety of methods, such as by using one or more scalpels or by a processing tool that automatically divides the tissue into particles of a desired size. Various suitable ways in which tissue may be harvested from a patient will be apparent to those of ordinary skill in the art in view of the teachings herein. The viable muscle tissue fragments may then be combined with a fluid carrier, and optionally other tissue healing agents or materials, etc., and injected into the reservoir (34) through the inlet port (36). Alternatively, one or more components of the tissue treatment composition may inserted into the reservoir (34) separately, rather than being combined externally of the reservoir. It should also be understood that any formulation of medical fluid described herein may be introduced into reservoir (34).

A tissue mincer may be provided within the stapler (20), such as in the reservoir (34), so that tissue specimens may be minced within the stapler. Such a configuration may facilitate the processing (e.g., mincing, etc.) of viable tissue specimens immediately prior to use. In addition, the number of implements needed would also be reduced. When a mincer is provided in the reservoir (34), the reservoir comprises a mincing chamber for mincing tissue fragments into even smaller fragments and containing the minced tissue fragments as part of a tissue treatment composition for delivery to the staple and/or cut line.

By way of example, the stapler (20) may include an impeller (44) mounted within the reservoir (34). The impeller (44) may be configured to mince one or more tissue fragments inserted into the reservoir (34) through the inlet port (36) so as to cut the tissue fragments into even smaller pieces. The impeller (44) may be driven by a motor (45) provided in handle (22), and an actuator (46) may be provided on the exterior of handle (22) for activating the motor (45) to drive the impeller (44) and mince tissue fragments. The mincer (44) will also serve to blend the tissue fragments and carrier (as well as any other healing agents and/or other treatment composition components, etc.) into a more homogeneous tissue treatment composition.

As an alternative to the motor driven mincer (44) depicted in FIG. 2A, any of a variety of other devices and structures suitable for cutting or dividing tissue into smaller fragments may be provided. Such alternative mincers may be manually or mechanically driven. For example, one or more manually driven cutting blades may be located in the reservoir (34) in order to mince tissue fragments therein.

Also in the present example, a piston (40) is provided within the reservoir (34) for expelling fluid from the reservoir through a fluid conduit. The piston (40) comprises a cylindrical member sized to sealingly and slidingly fit within a corresponding cylindrical portion of the reservoir (34). An o-ring (41) is provided about the exterior circumference of piston (40) in order to sealingly engage the interior wall of the cylindrical portion of the reservoir (34). The piston (40) may be mechanically or manually driven in order to expel fluid. In the present example, a slider (42) is provided on the exterior of the handle (22) and is attached to the piston (40) through an elongate slot (43) on the handle (22). By sliding slider (42) in the distal direction, the piston (40) will also move distally and expel fluid from the reservoir.

As best seen in FIGS. 2B-4, first (or fixed) clamping member (28) (also referred to as the stapling head) is located at the distal end of the shaft (24), and includes a plurality of deployable fasteners or staples (51) in one or more circular arrays. The first clamping member (28) also includes a hollow tubular casing (50) fixedly attached to the distal end of shaft (24). Tubular casing (50) is funnel-shaped, and slidably receives a staple driver (52) which can be advanced and retracted by operation of the trigger (23). The staple driver (52) includes a plurality of fingers (53) configured for engaging and distally driving the staples (51) from a staple holder (54) mounted at the distal end of the tubular casing (50). The staple holder (54) includes a plurality of staple receiving slots in which the staples (51) are positioned. A cylindrical knife (48) is mounted within the staple driver (52), coaxially inside of the array of staples (51), and may be advanced and retracted by the staple driver (52).

Movable second clamping member (30) includes a disk shaped anvil (56) rigidly attached to the distal end of a hollow anvil shaft (58). Staple forming pockets (59) are provided in at least one annular array around the periphery of the proximal end wall (57) of the anvil (56). The array of staple forming pockets (59) complements the array of staples (51) in the present example, such that the staple forming pockets (59) will be opposably aligned with the staples (51) in the fixed clamp member (28) when the movable second clamping member (30) moves from the open position of FIG. 3 to the closed position shown in FIG. 4. An anvil shroud (60) is attached to the distal end of anvil (56) in order to provide an atraumatic distal tip for the surgical stapler (20).

The anvil shaft (58) of the present example includes a bore (62) extending axially from the proximal end of anvil shaft (58), terminating at an end wall (64). One or more apertures (66) are arranged about the periphery of anvil shaft (58), and extend inwardly into bore (62). Apertures (66) may be located proximate to end wall (64) of anvil (56), as shown. As further described herein, tissue treatment composition in the reservoir (34) may be expelled from the interior of the anvil shaft (58) through apertures (66) so as to deliver the tissue healing agent(s) at the staple and/or cut line. The anvil shaft (58) may be detachably secured to post member (68), which is slidably supported by the first clamping member (28). The distal tip (69) of post member (68) is inserted into bore (62) of anvil shaft (58) in order to secure second clamping member (30) to post member (68), as shown in FIG. 3. One or more O-rings (70) or other seals may be provided about the circumference of post member (68) in order to removeably and sealingly secure post member (68) within bore (62). In addition, one or more circumferential grooves may be provided around the exterior surface of post member (68) and/or the interior surface of bore (62) to receive O-ring (70) therein. In order to further retain post member (68) within bore (62), one or more various retention features may be provided on post member (68) and/or anvil shaft (58). By way of example, and as depicted in U.S. Pat. No. 5,533,661, the post member (68) may have a reduced diameter portion that defines a shoulder that may be engaged by a corresponding structure provided within bore (62) of anvil shaft (58) (see, e.g., FIG. 2 of U.S. Pat. No. 5,533,661). Of course other features for retaining post member (68) within bore (62) will be apparent to those of ordinary skill in the art.

In the present example, the post member (68) is slidably received within a hollow central support tube (72) formed on the tubular casing (50) to allow longitudinal movement of the post member (68) relative to a staple holder (54) mounted at the distal end of the casing (50). One or more O-rings (74) or other seals may be provided about the circumference of the post member (68) in order to slidingly and sealingly position the post member within the central support tube (72). One or more circumferential grooves may be provided about the exterior surface of the post member (68) to receive O-rings (74) therein. The distal end of the central support tube (72) abuts against the proximal end surface of cylindrical knife (48), and the proximal end of the cylindrical knife (48) also includes an aperture through which the post member (68) extends.

In order to facilitate the insertion of the post member (68) into the anvil shaft (58), and to facilitate sliding movement of the post member (68) and the anvil shaft (58), the post member tip (69) has a frustoconical shape. In addition, the post member (68) includes a distal portion (76) having a smaller diameter than a proximal portion (77) of the post member. A tapered, frustoconical shoulder (78) may provide a smooth transition between the distal portion (76) and the proximal portion (77) of the post member (68). The outer circumference of at least the portion of the anvil shaft (58) mounted on the post member (68) may be approximately the same as the outer circumference of proximal portion (78) of post member (68). In addition, the proximal end wall (80) of the anvil shaft

(58) is tapered inwardly, as shown, so as to matingly engage shoulder (78) (see FIGS. 3 and 4). In this manner, when the anvil shaft (58) is mounted onto the distal portion (76) of the post member (68), the resulting assembly will have a generally constant diameter.

Figure 2B:
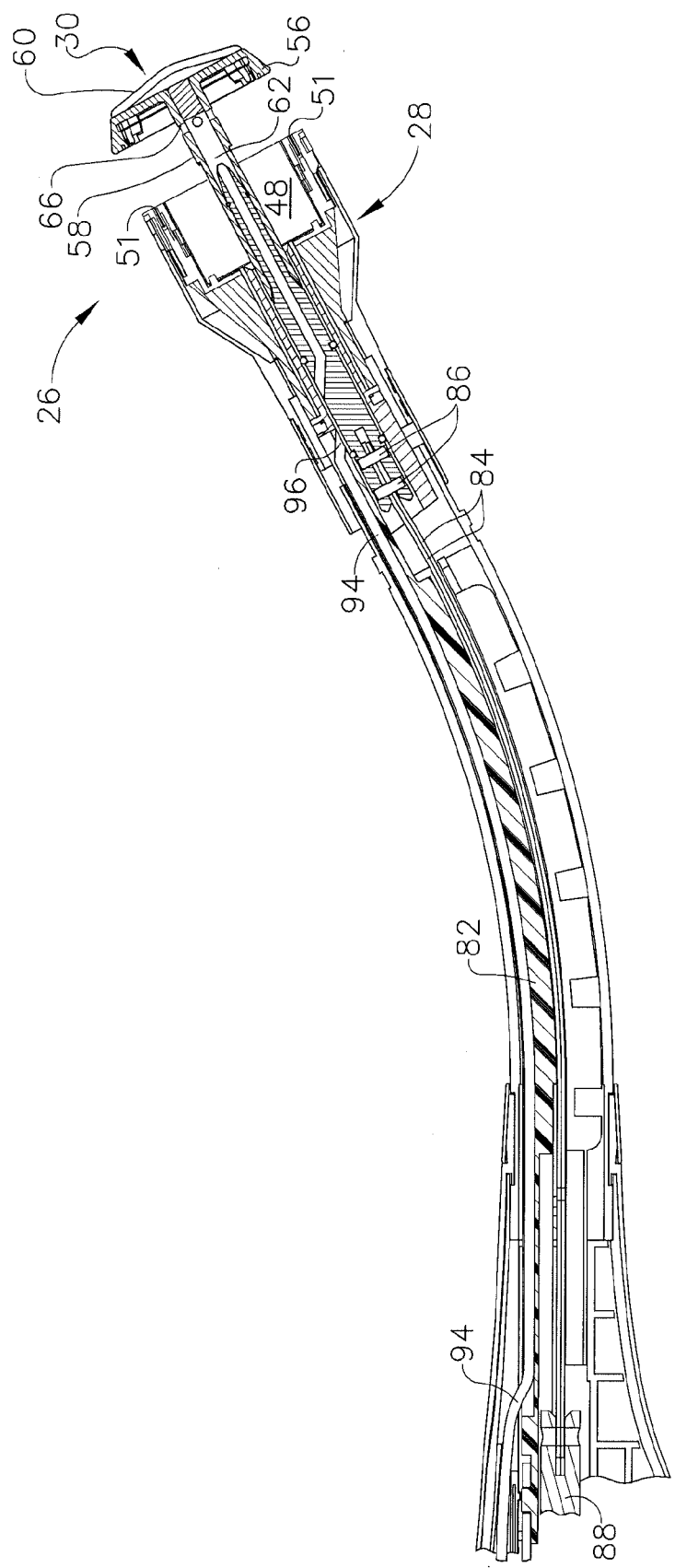
FIG. 2B depicts a partial cross-sectional view of a distal portion of the stapler shown in FIG. 1.

Referring to FIGS. 2A and 2B, a staple actuating member (82) is located within shaft (24) so as to extend between the trigger (23) and the staple driver (52). The staple actuating member (82) is configured to transmit actuating force from the trigger (23) to the staple driver (52) in order to urge staples (51) into the staple forming pockets (59) on the second clamping member (30). The proximal end of the staple actuating member (82) is positioned within the handle (22) and is coupled with the trigger (23) such that, when the trigger (23) is urged towards the handle (22), the staple actuating member (82) is urged distally within the shaft (24). The distal end of staple actuating member (82) is configured so as to engage staple driver (52), such that the distal movement of the staple actuating member (82) results in the firing of the staples (51). It should therefore be understood that stapler (50) may fire staples (51) in accordance with the teachings of one or more of U.S. Pat. Nos. 5,533,661, 6,193,129, 5,271,544, entitled "Surgical anastomosis stapling instrument," issued Dec. 21, 1993, and U.S. Pat. No. 7,506,791, entitled "Surgical stapling instrument with mechanical mechanism for limiting maximum tissue compression," issued Mar. 24, 2009, the disclosures of which are incorporated by reference herein. Of course, stapler (50) may alternatively fire staples (51) in any other suitable fashion as will be apparent to those of ordinary skill in the art in view of the teachings herein.

The shaft (24) of the stapler (20) also contains tension members (84) provided by a pair of elongated flexible bands for transmitting tension from the handle (22) to the second clamping member (30). The tension members (84) transmit motion from the handle (22) to allow the second clamping member (30) to be adjusted in position relative to the first clamping member (30). The distal ends of the tension members (84) are coupled with the post member (68) by a set of transverse pins (86). The proximal ends of the tension members (84) are coupled with the distal end of a control rod (88) in handle (22) by a transverse pin (89). The control rod (88) is located within handle (22) and is configured for longitudinal movement therein. The proximal end of the control rod (88) is threadingly coupled with the clamping knob (32). The clamping knob (32) is rotatably supported by the proximal end of the handle (22). An internally threaded sleeve (90) is provided at the distal end of clamping knob (32), and threadingly engages an elongated threaded shank (92) provided at the proximal end of the control rod (88). By rotating the clamping knob (32) in the counterclockwise direction (as viewed in FIG. 1), the threaded shank (92) will be pulled proximally into threaded sleeve (90), thus moving the control rod (88) and the tension members (84) in the proximal direction. To the extent that post member (68) and anvil shaft (58) are coupled together, the tension members (84) will likewise pull post member (68) and anvil shaft (58) in the proximal direction, thus pulling second clamping member (30) toward first clamping member (28) in order to clamp tissue to be stapled between the first and second clamping members (28, 30). Of course, any other suitable features, components, and methods may be used to pull second clamping member (30) toward first clamping member (28).

In order to deliver a tissue treatment composition (e.g., one or more tissue healing agents in a biocompatible fluid carrier, etc.) from reservoir (34) to a location between the first and second clamping members (28, 30), one or more fluid conduits may be provided within stapler (20). In the present example, a fluid conduit (94) extends from a bottom wall of the reservoir (34) through a portion of the handle (22), and through the interior of the shaft (24) to an open distal end (96) located within the central support tube (72). As best seen in FIGS. 3-4, a bore (98) extends axially through a portion of the post member (68), and includes an angled portion (99) that communicates between the axial portion of bore (98) and an orifice (100) provided on the exterior surface of the proximal portion (77) of the post member (68). The distal portion (76) of post member (68) includes an opening (102) that communicates with both the bore (98) of post member (68) and the bore (62) of the anvil shaft (58) when the latter is mounted on the post member (68). The size, location and configuration of fluid conduit (94), as well as bores (62, 98) and the apertures on bore (62), are merely exemplary. Any of a variety of alternatives may be readily employed in order to deliver a tissue treatment composition between the clamping members (28, 30) while not interfering with the stapling and cutting of tissue by the stapler (20).

Fluid conduit (94) and post member (68) are configured and positioned such that the open distal end (96) of fluid conduit (94) is selectively alignable with orifice (100) on the exterior of post member (68). In particular, in the present example, the fluid conduit (94) is configured such that the open distal end (96) of the fluid conduit will be aligned with orifice (100) on the post member (68) when second clamping member (30) is in the closed, or clamping, position depicted in FIG. 4. As described above, post member (68) is at a proximal position when second clamping member (30) is in the closed, or clamping, position. In this manner, fluid conduit (94) may be selectively in communication with the bore (62) of the anvil shaft (58) in order to selectively deliver fluid from the reservoir (34) to the apertures (66) provided about the periphery of anvil shaft (58). As mentioned previously, the apertures (66) on the anvil shaft (58) may be arranged about the periphery of the anvil shaft, proximally adjacent to end wall (57) of anvil (56). In this manner, fluid delivered from reservoir (34) may be expelled through the apertures (66) at the staple and/or cut line. In the present example, slider (42) is used to selectively expel fluid through the apertures (66). Thus, the end user may cause fluid to be expelled before, during or after stapling and/or before, during or after tissue cutting. Fluid may be expelled at multiple times, such as before stapling and after tissue cutting. Thus, a fluid tissue treatment composition in reservoir (34) may be urged through fluid conduit (94) and selectively expelled through the apertures (66), between the first and second clamping members (24, 25). When the second clamping member (30) is in the open position shown in FIG. 3, the bore (98) in the post member (68) will not be in communication with fluid conduit (94), and therefore fluid will not be expelled through the apertures (66) on anvil shaft (58).

In some versions, distal end (96) of fluid conduit (94) need not be precisely aligned with orifice (100) in order for medical fluid to be communicated from conduit (94) to bore (98). For instance, in some such versions, fluid may be communicated from conduit (94) to bore (98) as long as distal end (96) of conduit (94) is longitudinally positioned somewhere between the o-ring (74) that is distal to orifice (100) and the o-ring (74) that is proximal to orifice (100). Of course, these two o-rings (74) may be separated from each other by any suitable longitudinal distance, which may affect the range of longitudinal positions of post member (68) relative to conduit (94) at which medical fluid may be communicated from conduit (94) to bore (98). In some versions, distal end (96) of fluid conduit (94) must be aligned with orifice (100) in order for medical fluid to be communicated from conduit (94) to bore (98). It should also be understood that one or more additional o-rings (not shown) may be positioned about post member (68) and/or elsewhere to substantially fluidly isolate distal end (96) of fluid conduit (94) when post member (68) is at a distal position as shown in FIG. 3.

In the present example, and as mentioned previously, a piston (40) is provided within the reservoir (34) for expelling a tissue treatment composition or medical fluid (e.g., minced viable tissue fragments suspended in a biocompatible carrier, etc.) from the reservoir (34) through the fluid conduit (94). The piston (40) may comprise, for example, a cylindrical member sized to sealingly and slidingly fit within a corresponding cylindrical portion of the reservoir (34). By sliding slider (42) in the distal direction, the piston (40) will also move distally and expel fluid from the reservoir (34) through the fluid conduit (94), at least when the open distal end (96) of fluid conduit (94) is substantially aligned with orifice (100) on the exterior of post member (68) or is otherwise suitably positioned between o-rings (74). Of course, a tissue treatment composition may be delivered from the reservoir (34) through the fluid conduit (94) and expelled from the apertures (66) in a variety of other manners. For example, a selectively activatable pump may be provided in order to force the treatment composition through the conduit (94). Alternatively, the reservoir (34) may be pressurized such that, when the open distal end (96) of fluid conduit (94) is aligned with orifice (100) on the exterior of the post member (68), the treatment composition will be expelled from the apertures (66) provided about the periphery of the anvil shaft (58). Other suitable ways in which a tissue treatment composition may be delivered from the reservoir (34) through the fluid conduit (94) and expelled from the apertures (66) will be apparent to those of ordinary skill in the art in view of the teachings herein.

A. Exemplary Biocompatible Scaffold for Receiving Tissue Treatment Composition

Figure 5:
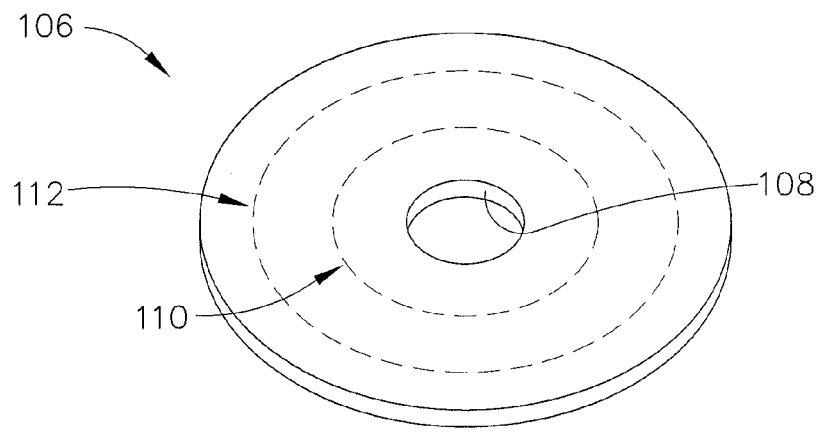
FIG. 5 depicts a perspective view of an exemplary scaffold for use with a circular stapler.

While fluid tissue treatment composition may simply be expelled between the clamping members (28, 30) in order to deliver one or more tissue healing agents, etc. at the suture and/or cutting line, a biocompatible scaffold (106) may be used to receive the tissue treatment composition between the clamping members (28, 30). As shown in FIGS. 3-5, scaffold (106) comprises an annular disc-shaped member that is positionable between the first and second clamping members (28, 30). The disc-shaped scaffold (106) includes a central aperture (108) sized so that the scaffold (106) may be positioned on anvil shaft (58), between the first and second clamping members (28, 30), as shown in FIG. 3. The central aperture (108) may be sized to snugly, yet slidably, fit onto the anvil shaft (58). In this manner, scaffold (106) may be positioned on anvil shaft (58) at any location that does not interfere with insertion of the end effector (26) into tissue lumens to be connected or the fitting of purse string sutures around the tissue lumens (as further described herein). When the second clamping member (30) is moved to the closed, or clamping position shown in FIG. 4, the scaffold (106) will slide along anvil shaft (58) until the scaffold abuts against the proximal end wall (57) of anvil (56), with central aperture (108) extending around the anvil shaft (58) at substantially the same longitudinal position as apertures (66). The tissue treatment composition may thus be expelled through apertures (66) around the circumference of central aperture (108), allowing scaffold (106) to absorb the tissue treatment composition.

The diameter of disc-shaped scaffold (106) may be chosen so that scaffold (106) will be stapled between the end walls of the tissue lumens. Thus, when scaffold (106) is positioned on anvil shaft (58), the outer perimeter of scaffold (106) will extend radially beyond the circular staple line. In other words, the diameter of scaffold (106) may be greater than the distance between the outermost staples (51) located on opposite sides of staple holder (54). In this manner, scaffold (106) will be held in place between the tissue ends by the formed staples.

While scaffold (106) is slid onto anvil shaft (58) prior to securing the anvil shaft over the post member (68) in the present example, the scaffold (106) includes a radial slit in some versions to allow the scaffold to be positioned on the anvil shaft (58) after the anvil shaft (58) has been attached to post member (68). Such a slit (not shown) may extend through the full thickness of the scaffold (106), from central aperture (108) to the outer circumference of the scaffold (106).

When positioned between the first and second clamping members (28, 30), scaffold (106) is positioned to receive the tissue treatment composition expelled through the apertures (66). When the tissue treatment composition includes viable tissue fragments, viable cells may migrate onto and/or into the scaffold (106), and thereafter may proliferate and integrate with tissue surrounding the stapled location. Scaffold (106) may be porous or non-porous. If desired, scaffold (106) may also be bioabsorbable. Scaffold (106) may alternatively be non-bioabsorbable so that it will remain stapled in place and continue to provide support at the staple location. Scaffold (106) may also be pliable to allow the scaffold (106) to adjust to the dimensions and/or configuration of the staple site.

By way of further example, scaffold (106) may be made from any of the variety of materials and methods, such as those described in U.S. Pub. No. 2004/0078090, the disclosure of which is incorporated by reference herein. By way of example only, scaffold (106) may be formed from a biocompatible polymer, injectable gel, ceramic material, autogeneic tissue, allogeneic tissue, xenogeneic tissue or combinations thereof. Biocompatible polymers may, for example, synthetic polymers, natural polymers and combinations thereof. Suitable biocompatible synthetic polymers can include, for example, polymers selected from the group consisting of aliphatic polyesters, poly(amino acids), polypropylene fumarate), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and blends thereof. Suitable synthetic polymers may also include biosynthetic polymers based on sequences found in collagen, elastin, thrombin, fibronectin, starches, poly(amino acid), gelatin, alginate, pectin, fibrin, oxidized cellulose, chitin, chitosan, tropoelastin, hyaluronic acid, ribonucleic acids, deoxyribonucleic acids, polypeptides, proteins, polysaccharides, polynucleotides and combinations thereof. Suitable biocompatible natural polymers may include, for example, fibrin-based materials, collagen-based materials, hyaluronic acid-based materials, glycoprotein-based materials, cellulose-based materials, silks and combinations thereof. In the present example, the biocompatible scaffold (106) can comprise freeze-dried fibrin. Still other suitable materials and combinations of materials that may be used to form at least part of scaffold (106) will be apparent to those of ordinary skill in the art in view of the teachings herein.

Scaffold (106) may also be anatomy specific in order to promote the regeneration of particular types of cells or structures. For example, it may be desirable to promote the regeneration of a structure such as a sphincter or valve that is resected in a patient (e.g., anal sphincter, pyloric sphincter, ileocecal valve, lower esophageal sphincter, etc.). In such instances, scaffold (106) may comprise one or more tissue specific components or materials that will particularly promote the regeneration of the resected sphincter or valve (or any of a variety of other anatomical structure). In addition or in the alternative, the tissue treatment composition applied to the scaffold (106) may be anatomically-specific, such as a suspension of stem cells that will regenerate a specific anatomical structure (e.g., a sphincter or valve) when applied to the scaffold (106) stapled between tissue in a patient.

Figure 18A:
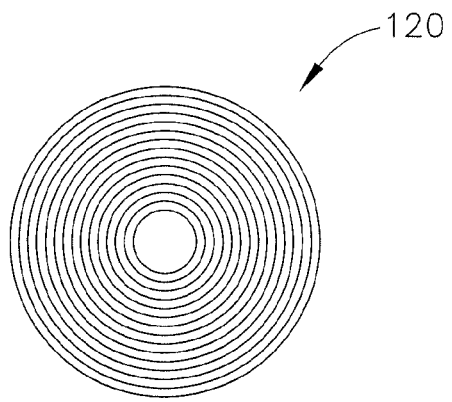
FIG. 18A depicts a top plan schematic view of another exemplary scaffold for use with a circular stapler.
Figure 18B:
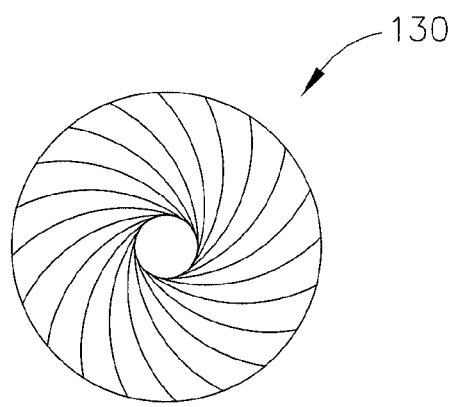
FIG. 18B depicts a top plan schematic view of yet another exemplary scaffold for use with a circular stapler.
Figure 18C:
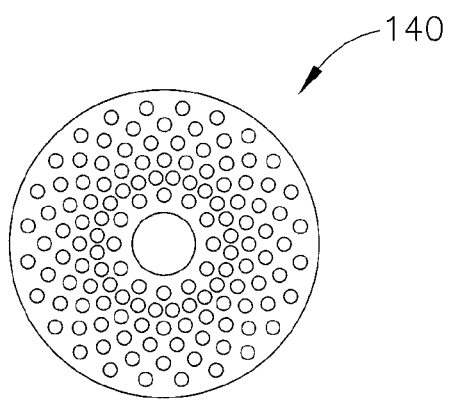
FIG. 18C depicts a top plan schematic view of still another exemplary scaffold for use with a circular stapler.

By way of further example, the scaffold may include one or more components such as fibers that are specifically arranged in the scaffold so as to direct the regeneration of cells in a particular orientation. In one version shown in the schematic illustration of FIG. 18A, scaffold (120) comprises fibers arranged in one or more circles concentrically arrayed about the central aperture of scaffold (120). Such an arrangement of the components used to form scaffold (120) may help to direct cell regeneration in a similar pattern. Of course the fibers may be arranged in any number of concentric circles or other patterns. A scaffold as shown in FIG. 18A may be useful, for example, in regenerating a sphincter. FIG. 18B schematically depicts another version of a scaffold (130) comprising fibers arranged in a plurality of concentric spirals emanating away from the central aperture of scaffold (130). FIG. 18C schematically depicts still another version of a scaffold (140) comprising fibers arranged in a plurality of circles arrayed about scaffold (140). Of course the fibers may be arranged in any of a variety of orientations, including, for example, a combination of one or more circles (concentric and/or non-concentric) and/or one or more spirals or other shapes in order to direct cell regeneration in a variety of different orientations.

It should also be pointed out that one or more scaffolds (106, 120, 130, 140, 206) may be shipped to end-users with stapler (20), such as in kit form. The scaffold(s) (106, 120, 130, 140, 206) may be separately packaged in a suitable sterile container(s), or a scaffold may be provided pre-installed on a stapler (20) between the first and second clamping members (28, 30).

B. Exemplary Use of Surgical Stapler in Combination with Biocompatible Scaffold

As mentioned previously, circular stapler (20) may be used to perform an anastomosis in which two lumens of tissue are attached together by one or more circular arrays of staples. By way of example only, and as depicted in FIGS. 3 and 4, first and second portions of intestinal lumen (116, 117), respectively, may be attached to one another following a resection. The stapler (20) may first be prepared for use by positioning the scaffold (106) on the anvil shaft (58) of the second clamping member (30), and thereafter sliding the anvil shaft (58) over the post member (68) as depicted in FIGS. 1-2 (where scaffold (106) has been omitted). Thereafter, the circular end effector (26) comprising first and second tissue clamping members (28, 30) is inserted into a longitudinal slit (not shown) within the first portion of intestinal tissue (116), and moved into the position shown adjacent to an open end of the tissue (116). The movable second clamping member (30) is moved to the open position and the second portion of intestinal tissue (117) is inserted over the second clamping member (30), as shown in FIG. 3. Thereafter, each portion of tissue (116, 117) is fitted with a purse string of suture (118) placed about the open ends of the intestinal tissue (116, 117). Each piece of suture (118) is drawn tight to close the open ends of intestinal tissue (116, 117), and tied for security.

After the purse strings (118) are tied, clamping knob (32) is rotated such that the movable second clamping member (30) is pulled toward first clamping member (28) to a position adjacent to the first clamping member (28) in order to clamp the first and second portions of intestinal tissue (116, 117) therebetween, with scaffold (106) clamped between the ends of the tissue (see FIG. 4). As the second clamping member (30) is pulled toward the first clamping member (28), and when open distal end (96) of fluid conduit is sufficiently aligned with orifice (100) of bore (98), a tissue treatment composition in reservoir (34) is urged through fluid conduit (94) so as to be expelled from the anvil shaft (58) through apertures (66) by pushing the lever (108) on the handle (22) distally towards the circular end effector (26). Alternatively, or in addition thereto, a tissue treatment composition may be expelled through the apertures (66) after the tissue portions (116, 117) and scaffold (106) have been clamped between first and second clamping members (28, 30). The treatment composition expelled through the apertures (66) and containing one or more healing agents will flow radially into and/or across the surface of the scaffold (106), impregnating the scaffold (106).

Thereafter, the circular stapling device (20) is fired by actuating the firing trigger (23). The ends of staples (51) are urged out of the staple holder (54), through the first portion of intestinal tissue (116), through the scaffold (106) along dashed staple line (112) (see FIG. 5), through the second portion of intestinal tissue (117), and against the staple forming pockets (59) of the anvil (56) in order to form the staples and staple tissue portions (116, 117) together (with scaffold (106) held therebetween). Cylindrical knife (48) is also advanced by the staple driver (52), through the first and second portions of intestinal tissue (116, 117), and through scaffold (106) along first dashed line (110) (see FIG. 5), interior of the staple line. The one or more healing agents absorbed into and/or on scaffold (106) are released along the staple line and the cut line in order to accelerate tissue healing and/or promote tissue regeneration. It should be noted that dashed cut line (110) and staple line (112) shown on scaffold (106) in FIG. 5 are merely included for reference, and do not necessarily represent any structure or feature on the scaffold.

Scaffold (106) will then remain in place between the first and second intestinal tissue portions (116, 117). If scaffold (106) is made from a bioabsorbable material, the scaffold (106) will be absorbed over time. If scaffold (106) is not made from a bioabsorbable material, it will remain in place as an annular ring and support the stapled connection between the tissue lumens (116, 117). Still other suitable ways in which stapler (20) may be used, either with or without scaffold (106), will be apparent to those of ordinary skill in the art in view of the teachings herein.

C. Exemplary Alternative Biocompatible Scaffold

Figure 6:
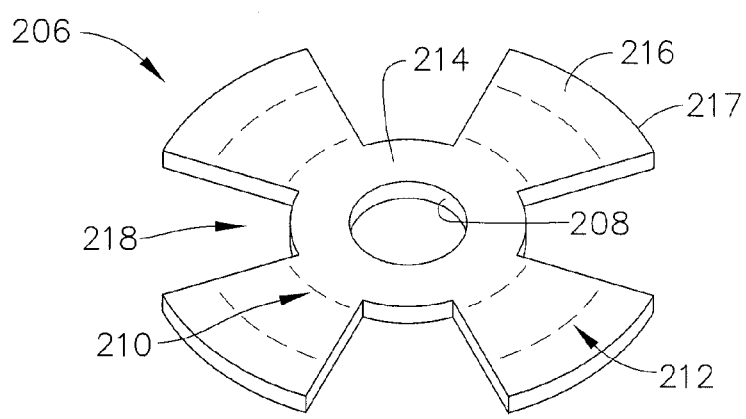
FIG. 6 depicts a perspective view of another exemplary scaffold for use with a circular stapler.

FIG. 6 depicts another exemplary biocompatible scaffold (206) that may be used in place of scaffold (106) described above. Scaffold (206) of this example may be made from any of the variety of materials mentioned previously for scaffold (106), such as freeze-dried fibrin, etc., or any other suitable material(s). Biocompatible scaffold (206) includes an annular disc-shaped portion (214), having a central aperture (208) extending therethrough, and a plurality of radially-extending tabs (216) extending radially away from the outer circumferential edge of disc-shaped portion (214). The outer arcuate edges (217) of the tabs (216) define an outer circumference of the scaffold (206) which may be sized similarly to that described for scaffold (106). Thus, biocompatible scaffold (206) may be viewed as an annular disc-shaped member having a plurality of radial cutouts (218) that define tabs (216) therebetween.

Scaffold (206) may be used in conjunction with a circular stapler such as surgical stapling instrument (20) in the same way described previously with respect to scaffold (106). In particular, central aperture (208) may be sized so that the scaffold (206) may be positioned on the anvil shaft (58), between the first and second clamping members (28, 30). Central aperture (208) also may be sized to snugly, yet slidably, fit onto the anvil shaft (58).

The annular disc-shaped portion (214) of scaffold (206), however, may have a diameter that is smaller than the diameter of the cylindrical knife (48) of stapler (20). Thus, the dashed cut line (210) shown in FIG. 6 is located outwardly of disc-shaped portion (214) such that the cut line (210) extends across each of the radially-extending tabs (216). When scaffold (206) is used in forming an anastomosis using surgical stapler (20) in the manner described previously, the radial tabs (216) of the scaffold (206) will be stapled between the tissue lumens along staple line (212), and the cylindrical knife (48) of the stapler (20) will cut through scaffold (206) along cut line (210). In this manner, the only portions of scaffold (206) that remain stapled between the tissue lumens will be the portion of each radial tab (216) extending between cut line (210) and the outer arcuate edge (217) of the tab. Since the radial tabs (216) of scaffold (206) will be spaced apart around the circumference of the junction between the two tissue lumens, the scaffold (206) will not interfere with peristalsis or other expansion or contraction of the lumen on which the anastomosis is formed. Of course, versions of scaffold (106) described above will not necessarily interfere with peristalsis once installed. By way of example only, the material(s) forming some versions of scaffold (106) may allow scaffold (106) to radially expand and contract freely during peristalsis. It should be understood that the presence and configuration of tabs (216) may allow a different selection of materials to compose scaffold (206) than might otherwise be available to compose scaffold (106) (e.g., non-stretchable materials, etc.).

Any number of radial tabs (216) may be provided on biocompatible scaffold (206). However, it may be desirable in some settings to space adjacent tabs (216) apart from one another to a degree where a formed staple will not span between adjacent tabs (216). In other words, the distance between adjacent radial tabs (216) at staple line (212) may be greater than the length of a formed staple. It will also be noted that radial tabs (216) may have any of a variety of sizes and shapes, and that shown is merely one embodiment. Likewise, while cutouts (218) are shown as having an angular width that approximately matches the angular width of tabs (216), it should be understood that cutouts (218) may have any other suitable angular width; and that the angular width of cutouts (218) may bear any suitable relationship with the angular width of tabs (216). In some versions, cutouts (218) are simply radial slits.

Biocompatible scaffold (206) may also be used with a conventional circular stapler that is not configured to deliver fluid media from a reservoir to the scaffold. For example, biocompatible scaffold (206) may be used with a circular stapler of the type shown and described in U.S. Pat. No. 6,193,129, entitled "Cutting Blade for a Surgical Anastomosis Stapling Instrument," issued Feb. 27, 2001, the disclosure of which is incorporated by reference herein. In some versions, instead of delivering a tissue treatment composition through the stapler (20) to scaffold (206), a tissue treatment composition (e.g., a suspension of minced viable tissue fragments, etc.) may be pre-associated with the scaffold (206). By way of example only, scaffold (206) may be impregnated and/or coated with a tissue treatment composition prior to or after being positioned on the anvil shaft of a circular stapler in the manner described previously. By way of further example, scaffold (206) may be formed of any of the materials and compositions described in U.S. Pub. No. 2004/0078090, the disclosure of which is incorporated by reference herein. Similarly, the tissue treatment composition associated with scaffold (206) may comprise, for example, any of the biological components and/or other compositions described in U.S. Pub. No. 2004/0078090 for application to the scaffolds described therein.

After the scaffold (206) having a tissue treatment composition is positioned on the anvil shaft of a conventional circular stapler, the tissue lumens to be stapled together may be clamped by the first and second clamping members, with the scaffold (206) positioned between the tissue portions to be joined. The stapler is then fired so as to staple and cut the tissue portions and scaffold (206). As described previously for use of scaffold (206) with stapler (20), the radial tabs (216) of scaffold (206) will remain in place between the joined tissue portions so as to allow the joined tissue to freely expand and contract. Other suitable ways in which scaffold (206) may be used will be apparent to those of ordinary skill in the art in view of the teachings herein.

III. Exemplary Rupturable Housing for Containing a Tissue Treatment Composition

As an alternative, or in addition to delivering a tissue treatment composition from a reservoir to the region between the stapling head and anvil of a surgical stapler, one or more rupturable fluid housings containing a tissue treatment composition may be provided. The tissue treatment composition may comprise, for example, one or more tissue healing agents such as viable tissue fragments and/or any other formulation of medical fluid described herein. In some versions, a rupturable housing may be configured as a rupturable, biocompatible pouch configured to be alignably positionable between the stapling head (first clamping member) and anvil (second clamping member) of a surgical stapler. In addition or in the alternative, one or more rupturable, biocompatible housings may be located in the end effector of a surgical stapler. The rupturable housing(s) may be supplied preloaded with a tissue treatment composition and/or may be configured to be supplied with a tissue treatment composition (or components thereof) at the time of use. For example, in some versions, the rupturable housing(s) may be injected or otherwise filled with one or more viable tissue fragments at the time of use (e.g., injecting the rupturable housing with minced tissue fragments harvested from the patient and suspended in a suitable carrier). Various examples of how such a rupturable housing may be provided will be described in greater detail below, while additional examples will be apparent to those of ordinary skill in the art in view of the teachings herein.

Figure 7:
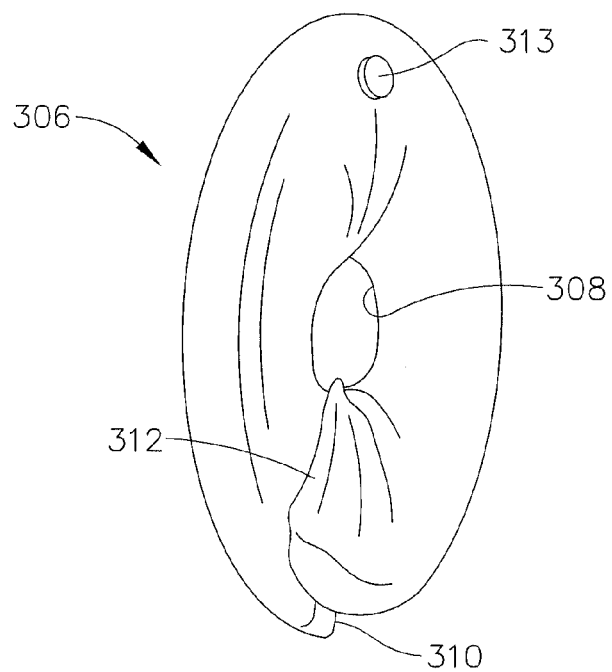
FIG. 7 depicts a perspective view of an exemplary rupturable fluid housing for use in performing an anastomosis.

A. Exemplary Rupturable Pouch Positionable between the Stapling Head and Anvil of a Surgical Stapler FIG. 7 depicts an example of a rupturable housing (306) for containing a tissue treatment composition, such as the various compositions described previously. Housing (306) comprises a rupturable, biocompatible, hollow pouch configured to be alignably positioned between the stapling head (or first clamping member) and anvil (or second clamping member) of a circular stapler. Pouch (306) includes a central aperture or groove (308) that is sized such that the pouch (306) may be positioned on, for example, an anvil shaft extending between the first and second clamping members of a circular stapler similar to the manner in which scaffolds (106, 206) may be mounted on an anvil shaft. Pouch (306) is rupturable such that, when positioned between the clamping members of a stapler and filled with a tissue treatment composition, pouch (306) will be ruptured by the firing of the staples and advancement of the stapler knife, which pierce pouch (306). In some versions, pouch (306) will also be ruptured when clamped between the clamping members just prior to stapling. Rupturing of pouch (306) will result in the release of the tissue treatment composition directly to the staple and cut lines. An annular ring portion of pouch (306) will also remain in place, fastened between the joined tissue portions by the staples, where it will reinforce the staple line as a buttressing material. If pouch (306) is made from a bioabsorbale material, the annular ring portion fastened between the joined tissue will be absorbed over time.

Figure 10:
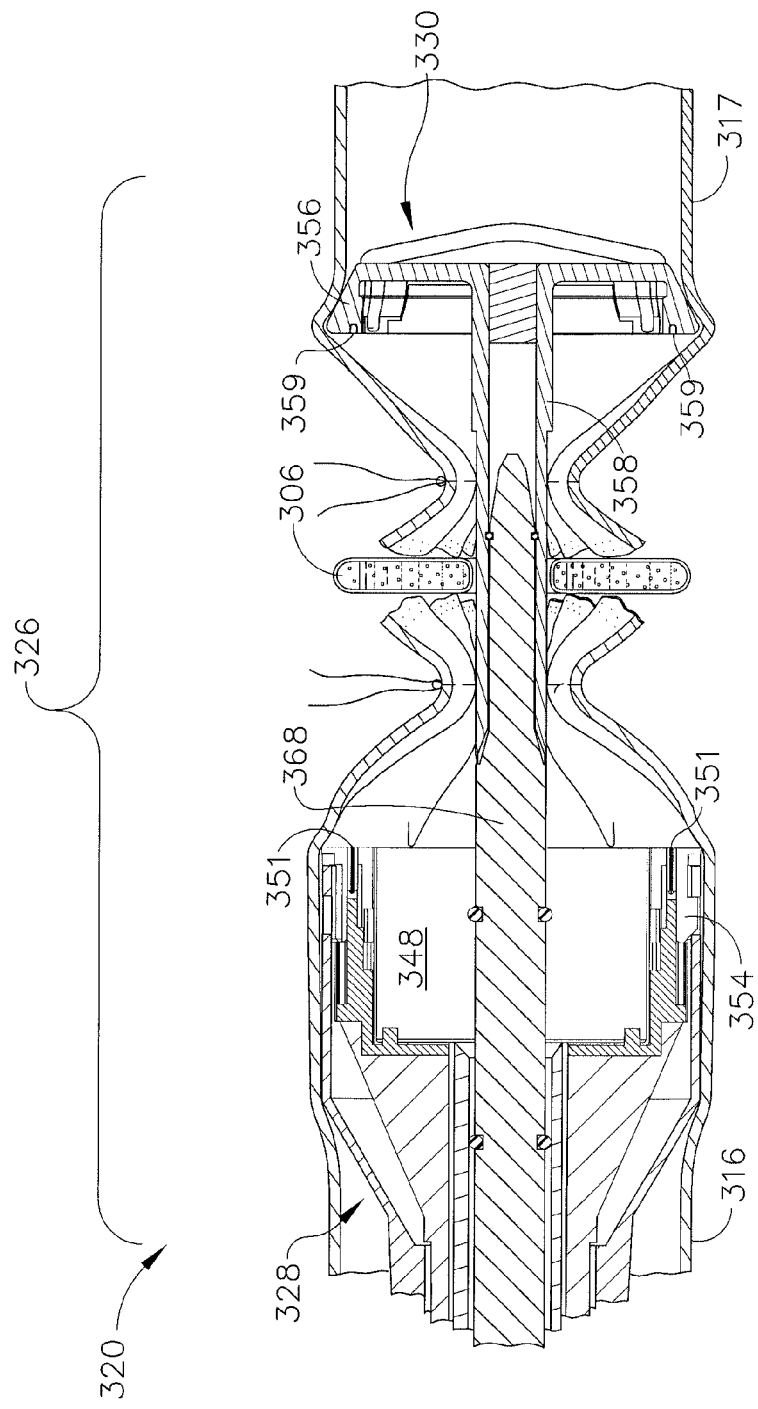
FIG. 10 depicts a partial cross-sectional view of the end effector portion of an exemplary circular surgical stapler positioned in a pair of tissue lumens to be joined in an anastomosis, with the fluid housing of FIG. 7 positioned between the clamping members.

Pouch (306) may be used in conjunction with, for example, circular stapler (20) described previously herein, or any of a variety of other circular staplers such as that shown and described in U.S. Pat. No. 6,193,129. Alternatively, and as further described below, FIG. 10, depicts rupturable pouch (306) alignably positioned between the first and second clamping members (328, 330) of an alternative version of a circular stapler (320), during the performance of an anastomosis. It should be noted that FIG. 10 depicts only the circular end effector portion (326) of the stapler (320). In this example, stapler (320) is similar in construction to stapler (20) described previously. However, stapler (320) of this example does not include a mincing reservoir, fluid passageway, or bore extending through the post member (368). Similarly, apertures are not provided on the anvil shaft (358) in this example, since stapler (320) is not configured for delivering a tissue treatment composition to the staple and/or cut line.

Like circular stapler (20) described previously and depicted in FIGS. 1-4, surgical stapler (320) shown in FIG. 10 includes a first clamping member (or stapling head)(328) and an opposed second clamping member (or anvil) (330) connected to a handle (not shown in FIG. 10). At least one of the tissue clamping members (328, 330) is movable between an open position for receiving tissue between the clamping members (328, 330), and a closed position for stapling tissue clamped between the clamping members (328, 330). The first clamping member (328) includes a plurality of staples (351) disposed therein, and the second clamping member (330) comprises an anvil (356) having staple forming pockets (359) for forming the staples (351). In the present example, the second clamping member (330) is moveable with respect to the first clamping member (328) along a longitudinal axis, and an anvil shaft (358) extends between the first and second clamping members (328, 330) along this longitudinal axis. As shown in FIG. 10, pouch (306) is configured to be alignably positioned between the first and second clamping members (328, 330) of stapler (320), mounted on anvil shaft (358).

The biocompatible pouch (306) may be configured in any of a variety of shapes suitable for housing a tissue treatment composition therein. For example, the pouch may be configured in the shape of, at least when filled with fluid, a toroid. If the toroid extends around in a complete circle (e.g., doughnut-shaped), a central aperture (308) will extend therethrough and the pouch (308) may simply be slid onto the anvil shaft (358) of the stapler (320) before the anvil shaft (358) is slid over the distal end of the post member (368). In this manner, the biocompatible pouch (308) may be alignably mounted on the anvil shaft (358) similar to the manner in which scaffold (106) described previously may be mounted on the anvil shaft of a circular stapler. Alternatively, the biocompatible pouch (306) may be configured as a doughnut-shaped toroid having a slit extending radially from the central aperture of the toroid to the outer circumference. In this configuration, the biocompatible pouch will be configured similar to a lock washer, and may be slid onto the anvil shaft (358) after the anvil shaft (358) has been attached to the post member (368), and even after the end effector (326) has been positioned within a pair of tissue lumens (316, 317) as shown in FIG. 10.

As shown in FIG. 7, biocompatible pouch (306) of the present example is configured as a spiral toroid having a central opening (308) extending therethrough. Pouch (306) is similar to the slit doughnut-shaped toroid described above. However the spiral toroid of FIG. 7 extends beyond one complete revolution such that the second radial end (312) of the spiral pouch overlaps the first radial end (310) of the spiral pouch. In some settings, this configuration may ensure release of the tissue treatment composition around the entire staple line; and may help to retain the fluid-filled pouch (306) on the anvil shaft (358). Biocompatible pouch (306) (as well as pouch (406) described in detail below) may be made from any of a variety of biocompatible materials, including bioabsorbable materials, which can be formed into a sealable housing that will not only contain fluid but also be rupturable. By way of example only, pouch (306, 406) may be made from polyglycoline (PGA), polylactide (PLA), polycaprolactone (PLC), polydioxanone (PDO), poly(lactide-co-glycolide) (PLGA), polyhydroxybutyrate (PHB), and/or polyhydroxyvalerate (PHV). Alternatively, any other suitable material or combination of materials may be used.

As mentioned previously, pouch (306) is configured to releasably contain a tissue treatment composition. Pouch (306) may be supplied preloaded with a tissue treatment composition, in which case pouch (306) may be provided as a sterile, sealed structure without a port or other means for adding materials thereto. Alternatively, pouch (306) may be configured to be filled with a tissue treatment composition (or components thereof) at the time of use. Pouch (306) may be supplied to the end-user partially-filled with one or more components of a tissue treatment composition (e.g., a suitable carrier solution), and the end-user may add additional components at the time of use (e.g., minced viable tissue fragments harvested, for example, from the patient with whom the pouch is to be used). Alternatively, pouch (306) may be supplied empty to the end-user, so that the end-user will fill pouch (306) with a tissue treatment composition (e.g., filling the pouch with minced viable tissue fragments harvested from the patient and suspended in a suitable carrier). In order to allow pouch (306) to be filled with a tissue treatment composition (or components thereof), particularly by an end-user such as a surgeon, a sealable port (313) may be provided on pouch (306). Sealable port (313) may be positioned at any of a variety of locations on pouch (306), and provides an inlet through which pouch (306) may be filled which materials such as tissue fragments. Port (313) may have any of a variety of configurations and structures. For example, port (313) may comprise a self-sealing septum made from a biocompatible material, such as an elastomer suitable for implantation in a patient.

In order for the pouch (306) to be penetrated by staples fired therethrough, when pouch (306) is positioned on anvil shaft (358) as shown in FIG. 10, the outer perimeter of pouch (306) may extend radially beyond the circular staple line. In other words, the diameter of scaffold (306) may be greater than the distance between the outermost staples (351) located on opposite sides of staple holder (354). In this manner, if not ruptured when clamped between the first and second clamping members, pouch (306) will be ruptured by staples (351) when the stapler is fired. In addition or in the alternative, pouch (306) may be sized such that when pouch (306) is positioned on anvil shaft (358) as shown in FIG. 10, the outer perimeter of scaffold (306) will extend radially outward sufficient to be cut by knife (348) but not to the circular staple line. In some such versions, the pouch (306) may not be ruptured by the staples, but will be ruptured by the knife (348) as it cuts the joined tissue portions located radially inward of the staple line.

While pouch (306) may be aligned on the anvil shaft (358) in the proper location, it may also be desirable to further ensure proper positioning of pouch (306). For example, a biocompatible adhesive may be applied to one or both surfaces of pouch (306) (e.g., the opposing surfaces of pouch (306) that will abut against the tissue lumen (316, 317) end walls during use). Alternatively, or in addition thereto, the pouch (306) may be configured such it may be sutured to one or both of the tissue lumens (316, 317).

Figure 8:
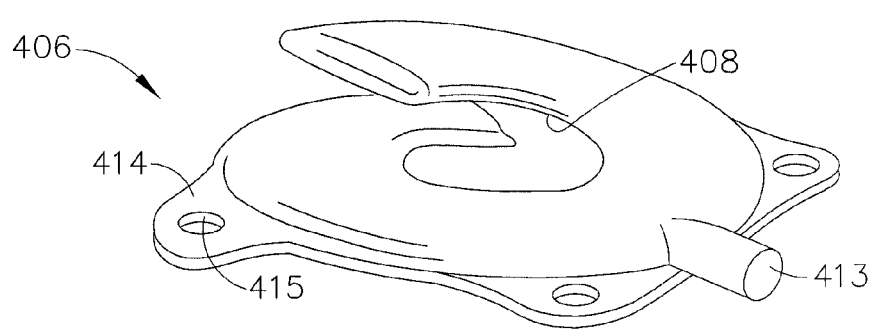
FIG. 8 depicts a perspective view of another exemplary rupturable fluid housing for use in performing an anastomosis.

FIG. 8 depicts another exemplary biocompatible pouch (406) that is configured to be attached to one or both tissue lumens via one or more stay sutures. Pouch (406) comprises a spiral toroid similar to pouch (306) in FIG. 7. Pouch (406) also includes a plurality of suturing tabs (414) arranged about the periphery of pouch (406). Each suturing tab (414) includes an aperture (415) extending therethrough. One or more stay sutures may be placed through apertures (415) in order to secure pouch (406) to one or both tissue lumens prior to performing an anastomosis. For example, pouch (406) may be attached with stay stutures to the open end of one or both of the tissue lumens prior to insertion of the end effector of the stapler into the tissue lumens. Once again, a biocompatible adhesive may also be provided on one both surfaces of pouch (406) in order to further secure the pouch (406) to the tissue lumens.

Pouch (406) having a tissue treatment composition contained therein may also be used to perform an anastomosis without the use of a circular stapler. For example, pouch (406) may be attached to one or both tissue lumens using one or more stay sutures and/or a suitable adhesive. Thereafter, a surgeon may then attach the open ends of the tissue lumens using, for example, conventional suturing. Pouch (406) may be ruptured to release the tissue treatment composition by the suturing process (e.g., by advancing the suturing needle through pouch (406)) and/or by use of a surgical implement such as a scalpel or clamp.

Figure 9:
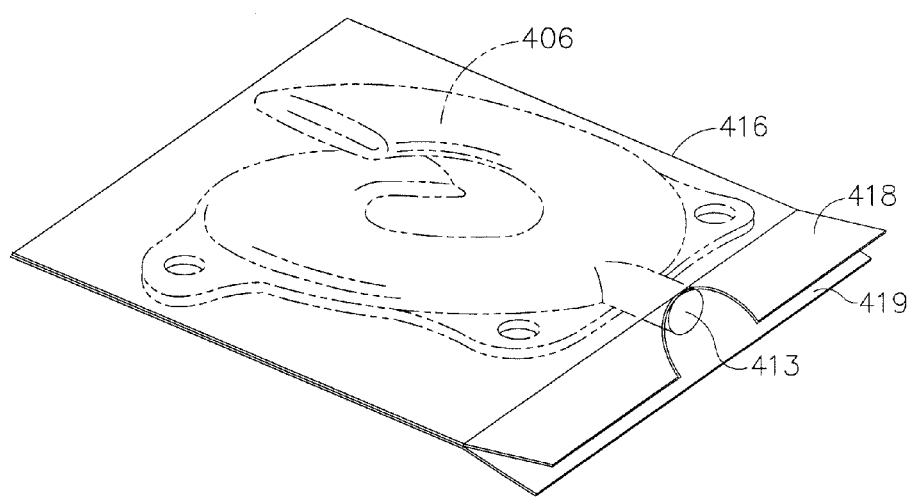
FIG. 9 depicts a perspective view of the rupturable fluid housing of FIG. 8 positioned in an exemplary package.

FIG. 9 depicts an example of a package (416) for pouch (306, 406). Package (416) may comprise, for example, an envelope made from opposed sheets of material sealed about their periphery. Portions of each sheet may remain unadhered along at least one edge thereof, so as to provide opposed flaps (418, 419). Flaps (418, 419) may be used to open package (416) by pulling flaps (418, 419) away from each other so as to separate the opposed sheets of material. In the present example, pouch (406) may be positioned within package (416) such that port (413), which extends away from an edge of pouch (406), is located between end flaps (418, 419). Such a configuration may allow the end-user to fill pouch (406) with fluid prior to opening package (416). Package (416) may be made of any of a variety of materials such as TYVEK.

As another merely illustrative example, rupturable pouch (306 or 406) may be configured similar to scaffold (206) and include an annular toroid-shaped portion (e.g., circular or spiral) and a plurality of radially-extending, hollow tab portions extending radially away from the outer circumferential surface of the toroid-shaped portion. Such a rupturable pouch may be sized such that, after stapled and cut between tissue lumens, only the tab portions will remain in place between the tissue lumens.

While the rupturable pouches (306, 406) described and depicted herein are designed for use with a circular stapler, a similar type of pouch may also be configured for use with a linear stapler such as that shown and described in U.S. Pat. Nos. 5,465,895, 6,964,363, and 6,978,921. By way of example, a biocompatible, rupturable pouch having a sealable port for filling with a tissue treatment composition may be configured as a sleeve that may be slid onto either or both of the tissue clamping members (e.g., the stapling head and/or the anvil) such that the pouch will be ruptured by being clamped between the tissue clamping members, by staples fired therethrough and/or by a knife of the stapler cutting the pouch. It should also be understood that a surgical stapler and a rupturable pouch may be provided to the end-user as a kit comprising the stapler and rupturable pouch, for the end-user to assemble these components together before use.

B. Exemplary Rupturable Housing Located on One or Both of the First and Second Clamping Members the End Effector of a Surgical Stapler As an alternative to using a rupturable biocompatible pouch alignably positionable between the first and second clamping members, or in addition thereto, a rupturable biocompatible housing for tissue treatment compositions may be provided on one or both of the first and second clamping members of a stapler. The rupturable housing(s) may be located so that the clamping of tissue prior to stapling and/or the firing of the staples will puncture the housing(s) and release the tissue treatment composition therefrom.

Figure 11:
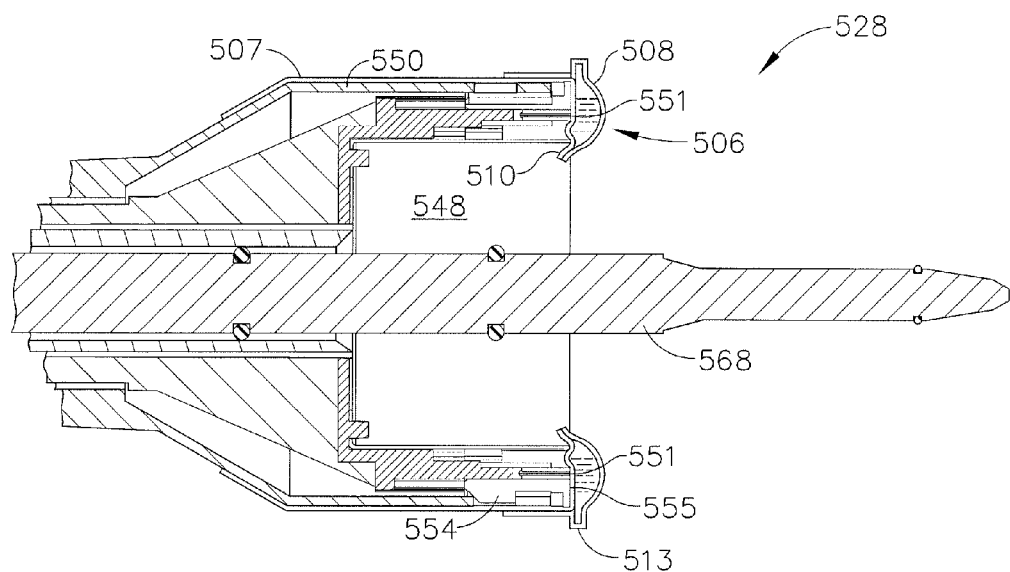
FIG. 11 depicts a partial cross-sectional view of an exemplary first clamping member of a circular surgical stapler with a rupturable fluid housing located on the clamping member.
Figure 12:
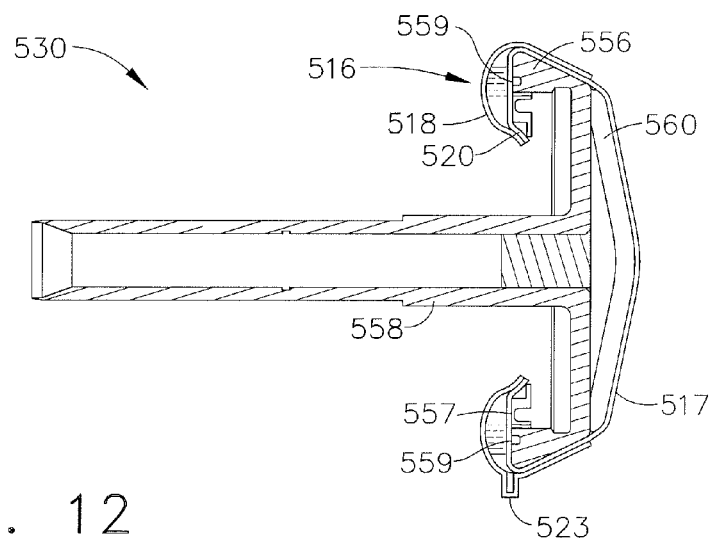
FIG. 12 depicts a partial cross-sectional view of an exemplary second clamping member of a circular surgical stapler with a rupturable fluid housing located on the clamping member.

FIGS. 11 and 12 depict exemplary first and second clamping members (528, 530) of a circular stapler. The first and second clamping members are similar in construction to that shown in FIG. 10, as well as FIGS. 1-4 (absent a bore in post member (568) for delivering fluid and apertures in anvil shaft (558) for expelling fluid). In the present example in FIG. 11, a rupturable, biocompatible housing (506) for releasably containing a tissue treatment composition is provided on first clamping member (528) as an annular ring-shaped housing that extends over the distal face (555) of staple holder (554). Since, when the stapler is fired, the staples (551) are driven distally away from the distal face (555) of staple holder (554), the staples (551) will be urged through rupturable housing (506), thereby causing the tissue treatment composition to be expelled from housing (506) at the staple line.

FIG. 12 shows an exemplary rupturable, biocompatible housing (516) for releasably containing a tissue treatment composition on second clamping member (530) as an annular ring-shaped housing that extends over the proximal end wall (557) of anvil (556). Since, when the stapler is fired, staples (551) are driven into the staple forming pockets (559) provided in proximal end wall (557) of anvil (556), staples (551) will be urged through rupturable housing (516), thereby causing the tissue treatment composition to be expelled from housing (516) at the staple line. One or both of the rupturable housings (506, 516) for releasably containing tissue treatment compositions may be provided on a surgical stapler. If both housings (506, 516) are provided, each may contain the same or different tissue treatment composition.

Rupturable housings (506, 516) may be provided on first and second clamping members (528, 530), respectively, in a variety of ways. For example, each housing (506, 516) may simply comprise a biocompatible ring-shaped housing that is adhesively attached to the indicated end surface (555, 557) of its respective clamping member (528, 530). In the present example, ports (513, 523) are also be provided on rupturable housings (506, 516), respectively, in order to allow an end-user to fill housings (506, 516) with tissue treatment composition(s). By way of example, each port (513, 523) may comprise a self-sealing structure, such as a biocompatible, self-sealing septum through which tissue treatment compositions (or components thereof) may be injected using, for example, a syringe. Of course, ports (513, 523) are merely optional. For instance, either or both of rupturable housings (506, 516) may be pre-filled with medical fluid(s). As another merely illustrative example, one of rupturable housings (506, 516) may be provided pre-filled with one or more medical fluid components; while the other of rupturable housings (516, 506) may be filled with one or more medical fluid components via a port (523, 513) just prior to deployment within the patient.

It should also be understood that one or both of rupturable housings (506, 516) may be formed by applying one or more biocompatible polymeric films (or other similar materials) to the ends of the first and second clamping members (528, 530). For instance, rupturable housing (506) on first clamping member (528) may be formed by adhering a first polymeric film layer (507) over the distal end of first clamping member (528), and thereafter selectively adhering a second polymeric film layer (508) to portions of first polymeric film layer (507) so as to form a fluid-fillable space between first and second polymeric film layers (507, 508) that defines housing (506). The first polymeric film layer (507) may be adhered about at least a portion of the tubular casing (550) of the first clamping member (528), as well as over the distal face (555) of staple holder (554) so as to cover staples (551) in staple holder (554). An inner end portion (510) of the first polymeric film layer (507) may extend radially into the interior of cylindrical knife (548), as shown. The second polymeric film layer (508) may then be selectively adhered to at least a portion of the first polymeric film layer (507) that is adhered to tubular casing (550), and to the distal end portion (510) of the first polymeric film layer (507). In the present example in FIG. 11, the first and second polymeric film layers (507, 508) are not adhered to one another where the first polymeric film layer (507) extends across the distal face (555) of the staple holder (554). This non-adhered, annular region between the first and second polymeric film layers (507, 508) thus defines rupturable housing (506) that may be filled with a tissue treatment composition. The polymeric film layers (507, 508) may be adhered to the various portions of the clamping members and each other in any of a variety of ways known to those skilled in the art such as using adhesive, heat welding, and/or ultrasonic welding, etc.

Rupturable housing (516) on second clamping member (530) may be formed in a similar fashion. For example, a first polymeric film layer (517) may be adhered to the outer surface of the anvil shroud (560), the exterior circumference of anvil (556), and the end wall (557) of the anvil (556) so as to extend over staple forming pockets (559). A second polymeric film layer (518) may then be selectively adhered to at least a portion of the first polymeric film layer (517) that is adhered to the exterior circumference of anvil (556), and to an inner end portion (520) of the first polymeric film layer (517) located radially inward of end wall (557) of anvil (556). In the present example in FIG. 12, the first and second polymeric film layers (517, 518) on second clamping member (530) are not adhered to one another where the first polymeric film layer (517) extends across the end wall (557) of the anvil (556). This non-adhered, annular region between the first and second polymeric film layers (517, 518) thus defines rupturable housing (516) that may be filled with a tissue treatment composition.

It will be understood that first and second polymeric film layers (507, 508) may comprise two separate films or may comprise a single continuous film that is folded over to provide the first and second film layers (507, 508). Similarly, first and second polymeric film layers (517, 518) may comprise two separate films or may comprise a single continuous film that is folded over to provide the first and second film layers (517, 518). As yet another merely illustrative alternative, housings (506 and/or 516) may be formed using a single polymeric film layer adhered to the respective first or second clamping member (528, 530) such that the housing comprises a non-adhered region between the polymeric film layer and the face of the clamping member (528, 530) to which it is attached.

Polymeric film layers (507, 508, 517, 518) may be made from any of a variety of biocompatible materials, including bioabsorbable materials, which can be formed into a film. By way of example only, the film layers (507, 508, 517, 518) may be made from polyglycoline (PGA), polylactide (PLA), polycaprolactone (PLC), polydioxanone (PDO), poly(lactide-co-glycolide)(PLGA), polyhydroxybutyrate (PHB), and/or polyhydroxyvalerate (PHV). Alternatively, any other suitable material or combination of materials may be used.

Rupturable housings (506, 516) may be filled with tissue treatment compositions using a syringe and needle. For example, the polymeric film layers used to form housings (506, 516) may be made from a self-sealing material such that a sufficiently small gauge needle inserted therethrough for filling the housings with fluid will not rupture or otherwise affect the integrity of housings (506, 516) and their ability to retain fluid therein. In order to provide a suitable injection site, a spacer (not shown) may be secured between the first and second polymeric film layers to as to define a region where the first and second polymeric films are spaced apart from one another (e.g., at locations (513 and 523) in FIGS. 11 and 12, respectively). By providing a small region where the polymeric films are spaced apart, a hollow injection space is provided for the injection of tissue treatment composition. Alternatively, a self-sealing septum or other suitable port may be provided on the anvil (556), in communication with housing (506) for filing the housing with a tissue treatment composition. Other suitable configurations and relationships for rupturable housings (506, 516) will be apparent to those of ordinary skill in the art in view of the teachings herein.

C. Exemplary Rupturable Housing Located in the End Effector of a Surgical Stapler As yet another alternative to using a rupturable biocompatible pouch alignably positionable between the first and second clamping members, or in addition thereto, a one or more rupturable biocompatible housings for tissue treatment compositions may be provided in the end effector of a surgical stapler. The rupturable housing(s) may be located so that the firing of a knife for cutting joined tissue will puncture the housing(s) and release the tissue treatment composition therefrom. For instance, FIGS. 13-15 depict a merely illustrative example of the end effector (626) of a circular stapler. The first and second clamping members (628, 630) are similar in construction to that shown in FIG. 10, as well as FIGS. 1-4 (absent a bore in post member (568) for delivering fluid and apertures in anvil shaft (558) for expelling fluid). However, a rupturable, biocompatible housing (606) for releasably containing a tissue treatment composition is provided in a chamber (608) defined in the anvil (656) of second clamping member (630). Chamber (608) has an open proximal end, and is located within the array of staple forming pockets (659) extending around proximal end wall (657) of anvil (656). Chamber (608) may be provided in any of a variety of shapes, such as the circular cup-shaped configuration shown in FIGS. 13-15, or any other suitable shape. The anvil shaft (658) extends through the center of chamber (608), into a spring cavity (616) extending distally away from the bottom of chamber (608). As with previous examples, anvil shaft (658) may be used to operatively attach second clamping member (630) to a post member (668) of the first clamping member (628).

Housing (606) may comprise a rupturable, flexible pouch sized and configured to fit into chamber (608). Thus, in the present example in FIGS. 13-15, housing (306) comprises a toroid (doughnut-shape) positioned in chamber (608), with the anvil shaft (658) extending through the central aperture of the toroid. Of course any of a variety of other shapes may be employed for housing (606). In order to facilitate the release of tissue treatment composition from housing (606) when the housing is ruptured, a fluid treatment composition may be pressurized in housing (606). Pressurization may be provided in a variety of ways. In the present example, housing (606) is spring pressurized by a proximally biased pressure plate (610). Pressure plate (610) of this example comprises an annular disc-shaped member positioned at the bottom (i.e., distal end surface) of chamber (608), with anvil shaft (658) extending through a central aperture (611) in pressure plate (610). Pressure plate (610), including its aperture (611), is sized such that pressure plate (610) may slidably move in the proximal direction (towards first clamping member (628)) along anvil shaft (658). Pressure plate (610) is spring-biased toward first clamping member (628) by a spring (618) extending around the distal end of anvil shaft (658) within spring cavity (616). Of course, pressure plate (610) may be biased in any other suitable fashion using any other suitable features or components.

In order to retain housing (306) within chamber (608) of the anvil (656), a stationary retention plate (612) is also provided in the present example. Retention plate (612) comprises an annular disc-shaped member positioned on anvil shaft (658), as shown. A shoulder (614) is provided on the anvil shaft (658) such that retention plate (612) rests on shoulder (614) within chamber (608). Rupturable housing (306) is located within chamber (608) of anvil (656) between pressure plate (610) and retention plate (612). Spring (608) urges pressure plate (610) against housing (606).

Retention plate (612) of the present example also includes a plurality of slots (613) extending through the thickness of retention plate (612) and angularly arrayed around the circumference of plate (612) adjacent its outer periphery. As described in more detail below, slots (613) are sized and configured such that a plurality of spikes (649) provided on the circular knife (648) of first clamping member (628) may be advanced through slots (613) in order to rupture housing (606) and release tissue treatment composition contained therein. The tissue treatment composition will then flow through slots (613), with spring-biased pressure plate (610) helping to expel the treatment composition from the ruptured housing (606). As a merely illustrative alternative to providing slots (613) in retention plate (612), retention plate (612) may be sized so that the spikes provided on knife (648) for rupturing housing (606) may be advanced past the outer circumference of retention plate (612) and into housing (606). Housing (606) may be made from any of a variety of biocompatible materials, including bioabsorbable materials, which can be formed into a sealable housing that will not only contain fluid but also be rupturable. By way of example only, housing (606) may be made from polyglycoline (PGA), polylactide (PLA), polycaprolactone (PLC), polydioxanone (PDO), poly(lactide-co-glycolide)(PLGA), polyhydroxybutyrate (PHB), and/or polyhydroxyvalerate (PHV). Alternatively, any other suitable material or combination of materials may be used to form housing (606).

Cutting knife (648) may be provided in first clamping member (628) in the manner described previously with respect to FIGS. 1-4. In order to allow knife (648) to rupture housing (606), a plurality of spikes (649) are provided on the knife (648) so as to extend distally away from the cutting edge (655) of the knife (648). Spikes (649) are located so as to be aligned with the slots (613) in retention plate (612) of the second clamping member (630). In this manner, when the stapler is fired and the knife (648) cuts through the portions of the joined tissue lumens (116, 117) interior of the staple line, spikes (649) on knife (648) will pass through the slots (613) of retention plate (612) to rupture housing (606). Spikes (649) may be added to the cutting edge (655) of a circular knife of the type shown in FIG. 3. Such an embodiment is shown, for example, in U.S. Pat. No. 6,193,129, the disclosure of which is incorporated by reference herein. It should be noted that additional spikes may be provided on the knife than is shown in U.S. Pat. No. 6,193,129, if desired, in order to facilitate housing puncture and release of tissue treatment composition around the entire cut and staple lines.

In the present example in FIGS. 13-17, cutting knife (648) not only has a plurality of spikes (649) extending distally away from the cutting edge (655), knife (648) is also fluted. Thus, cutting edge (655) is also fluted so as to provide a longer, and irregular cutting edge as compared to a conventional circular knife in a surgical stapler. In this manner, cutting edge (655) will mince the cut tissue into smaller pieces than the circular cutting edge shown on knife (48) of FIG. 3. The resulting tissue fragments may combine with the tissue treatment composition (which may also contain viable tissue fragments) expelled from housing (606) to promote healing and tissue regeneration. The tissue treatment composition in housing (606) may also contain one or more agents (e.g., fibrin, etc.) that help to maintain the tissue fragments cut by knife (648) at the cut line. In this manner, viable cells may migrate from the cut tissue fragments into the tissue surrounding the cut and staple lines.

Figure 16:
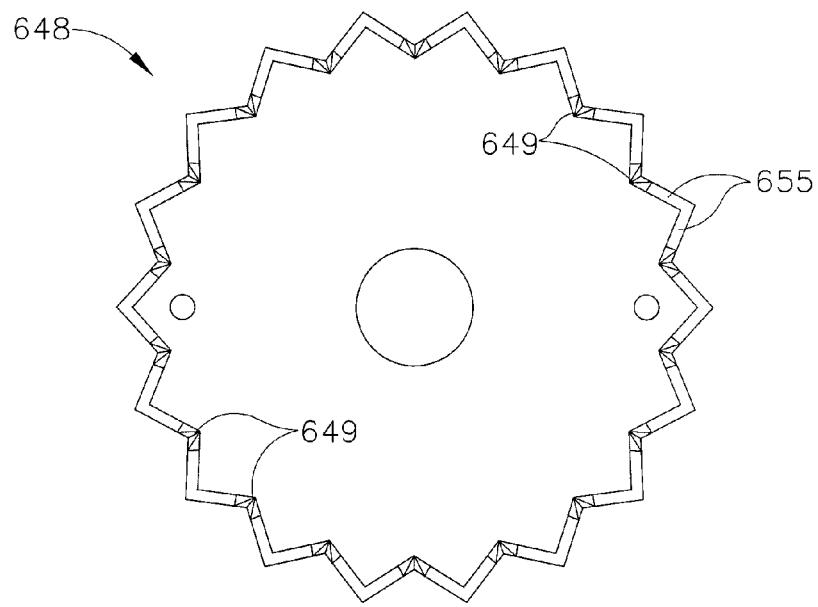
FIG. 16 depicts a top plan view of the fluted knife of the stapler shown in FIG. 13.
Figure 17:
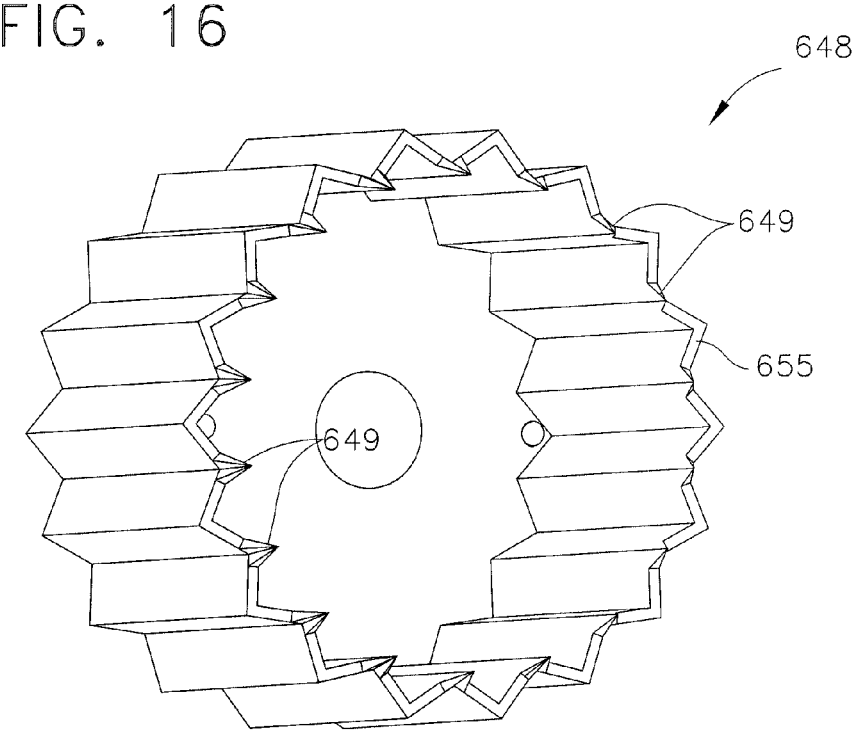
FIG. 17 depicts a perspective view of the fluted knife shown in FIG. 16.

Any of a variety of other non-circular, irregular shapes may be employed for the cutting knife (648) in place of, or in addition to, the fluted arrangement depicted in FIGS. 16-17. For example, the cutting edge (655) of cutting knife (648) may be configured in the shape of a star, a hexagon, an octagon, a polygon, or any other non-circular shape. In other examples, the cutting knife (648) may be configured such that a plurality of cutting edges (655) are provided, in any of a variety of one or more geometric shapes, with some of the cutting edges (655) arrayed radially inward of the outer perimeter of cutting knife (648). In still other examples, the cutting edge (655) may be serrated. In the present example, spikes (649) extend distally away from cutting edge (655) at the interior fold of each flute. Of course, spikes (649) may be located at any of a variety of other locations on knife (648) so as to be alignable with the slots (613) in retention plate (612). Other suitable configurations will be apparent to those of ordinary skill in the art in view of the teachings herein.

An exemplary use of a stapler having a rupturable housing (606) located in the end effector (626) to perform an anastomosis is shown sequentially in FIGS. 13-15, in which two lumens of tissue (116, 117) are attached together by one or more circular arrays of staples (651). The stapler may be provided to the end-user with housing (606) already filled with a tissue treatment composition. Alternatively, housing (606) may be empty or only partially filled with one or more components of the tissue treatment composition. The end-user (e.g., a surgeon) may then fill housing (606) (or add additional materials thereto) by, for example, injecting material (e.g., minced viable tissue fragments in a carrier, etc.) through one or more of the slots (613) in retention plate (612) or in any other suitable fashion. Housing (606) may be made from a self-sealing material such that a sufficiently small gauge needle inserted therethrough for filling the housing with fluid will not rupture or otherwise affect the integrity of housing (606) and its ability to retain fluid therein. Alternatively, a self-sealing septum or other suitable port may be provided on the anvil (656), in communication with housing (606) for filling the housing with a tissue treatment composition.

After the first and second clamping members (628, 630) have been attached to one another (if provided to the end-user in detached form), the circular end effector (626) comprising first and second tissue clamping members (628, 630) may be inserted into a longitudinal slit (not shown) within the first portion of intestinal tissue (116), and moved into the position shown adjacent to an open end of the tissue (116). The movable second clamping member (630) may be moved to the open position and the second portion of intestinal tissue (117) may be inserted over the second clamping member (630), as shown in FIG. 13. Thereafter, each portion of tissue (116, 117) may be fitted with a purse string of suture placed about the open ends of the intestinal tissue (116, 117), as described previously.

After the purse strings are tied, the movable second clamping member (630) is pulled towards first clamping member (628) to a position adjacent to the first clamping member (628) in order to clamp the first and second portions of intestinal tissue (116, 117) therebetween. As described previously, this may be accomplished, for example, by rotating a clamping knob or through use of another mechanism provided on the stapler. Once the ends of the tissue lumens are clamped between the first and second clamping members (628, 630) (e.g., similar to what is depicted in FIG. 4, with or without a scaffold positioned between the ends of the tissue lumens), the circular stapling device is fired such as by actuating a firing trigger provided on a staple handle. The ends of staples (651) are urged distally out of the staple holder (654), through the first portion of intestinal tissue (116), through the second portion of intestinal tissue (117), and against the staple forming pockets (659) of the anvil (656) in order to form the staples and fasten tissue portions (116, 117) together as shown in FIG. 14.

Knife (648) is also advanced by the staple driver (652), through the first and second portions of intestinal tissue (116, 117), interior of the staple line. The spikes (649) extending distally away from the cutting edge (655) of the knife (648) will pass through slots (613) of the stationary retention plate (612) in anvil (656), and will puncture housing (606) as shown in FIG. 14. Spring-biased pressure plate (610) will then urge the tissue treatment composition out of housing (606), through slots (613). In addition, the fluted cutting edge (655) of knife (648) will cut the portions of tissue lumens (116, 117) located between the staple line and the anvil shaft (658) into small fragments. Retention plate (612) may also act as a backstop or cutting surface, against which knife (648) will cut the tissue. In order to further mince the tissue fragments, knife (648) may be reciprocated any number of times to further mince the tissue fragments into even smaller pieces. This may be accomplished, for example, by releasing the trigger of the stapler so that the cutting edge (655) of knife (648) will move proximally away from retention plate (612), while still maintaining the clamping members (628, 630) in the closed position with the stapled tissue clamped therebetween, and thereafter firing the stapler again so as to distally advance the cutting edge (655) against the retention plate (612). This may be repeated any number of times to mince the cut tissue into suitably small fragments. The tissue fragments will combine with the tissue treatment composition released from housing (606) into the region between the first and second clamping members (628, 630), so that the tissue treatment composition and minced viable tissue fragments will be applied along to the tissue lumens at and around the cut line in order to accelerate tissue healing and promote tissue regeneration. Other suitable ways in which a stapler having end effector (626) as described above may be used will be apparent to those of ordinary skill in the art in view of the teachings herein.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of the devices described above may be actuated mechanically or electromechanically (e.g., using one or more electrical motors, solenoids, etc.). However, other actuation modes may be suitable as well including but not limited to pneumatic and/or hydraulic actuation, etc. Various suitable ways in which such alternative forms of actuation may be provided in a device as described above will be apparent to those of ordinary skill in the art in view of the teachings herein.

Versions of the devices described above may have various types of construction. By way of example only, any of the devices described herein, or components thereof, may be constructed from suitable metals, ceramics, plastics, or combinations thereof. Furthermore, although not required, the construction of devices described herein may be configured to be compatible with or optimize their use with various imaging technologies. For instance, a device configured for use with MRI may be constructed from all non-ferromagnetic materials. Also for instance, when using optional imaging technologies with devices described herein, certain configurations may include modifications to materials of construction such that portions or the device may readily appear in a resultant image. Various suitable ways in which these and other modifications to the construction of devices described herein may be carried out will be apparent to those of ordinary skill in the art in view of the teachings herein.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapling instrument for stapling tissue, comprising:
   (a) a handle portion;
   (b) first and second opposed clamping members coupled with the handle portion, at least one of the clamping members being movable between an open position for receiving tissue and a closed position for stapling tissue between the clamping members, wherein the first clamping member is configured to receive a plurality of staples, wherein the second clamping member comprises an anvil for forming the staples;
   (c) a reservoir configured to hold a tissue treatment composition, wherein the reservoir includes a mincing chamber having a mincer for mincing tissue fragments of a tissue treatment composition contained in the reservoir; and
   (d) a fluid conduit for selectively delivering a tissue treatment composition from the reservoir to a region between the first and second clamping members.

2. The surgical stapling instrument of claim 1, further comprising a shaft extending between the handle portion and the first and second clamping members, wherein the reservoir is provided in said handle portion, wherein the fluid conduit extends from the reservoir through the interior of the shaft.

3. The surgical stapling instrument of claim 1, further comprising an actuator for causing the mincer to mince tissue fragments within the reservoir.

4. The surgical stapling instrument of claim 1, further comprising a biocompatible scaffold positionable between the first and second clamping members, wherein the scaffold is configured to receive a tissue treatment composition delivered to the region between the clamping members.

5. The surgical stapling instrument of claim 4, further comprising an end effector shaft extending between the first and second clamping members, wherein the scaffold comprises an annular disc positionable between the first and second clamping members on the shaft.

6. The surgical stapling instrument of claim 1, further comprising an end effector shaft extending between the first and second clamping members, wherein the end effector shaft includes a bore extending through at least a portion of the end effector shaft and at least one aperture communicating between the bore and the exterior of the end effector shaft, wherein the bore is configured for selective fluid communication with the fluid conduit such that, when the bore is in fluid communication with the fluid conduit, a fluid treatment composition urged through the fluid conduit is expelled from the at least one aperture to a region between the first and second clamping members.

7. The surgical stapling instrument of claim 6, wherein the end effector shaft comprises:
   (i) an anvil shaft extending proximally away from the second clamping member, wherein a first part of the bore is formed through the anvil shaft, and
   (ii) a post member extending distally away from the first clamping member, wherein the second part of the bore is formed through the post member.

8. The surgical stapling instrument of claim 7, wherein the anvil shaft is configured to insertingly receive the post member.

9. The surgical stapling instrument of claim 7, wherein the post member is operably movable within the first clamping member to selectively place the bore in fluid communication with the fluid conduit.

10. The surgical stapling instrument of claim 6, wherein the bore and the fluid conduit are configured and positioned such that the bore is in fluid communication with the fluid conduit when the first and second clamping members are at the closed position.

* * * * *